United States Patent
Shen et al.

(10) Patent No.: US 11,944,452 B2
(45) Date of Patent: Apr. 2, 2024

(54) METHODS AND SYSTEMS TO MEASURE AND EVALUATE STABILITY OF MEDICAL IMPLANTS

(71) Applicant: UNIVERSITY OF WASHINGTON, Seattle, WA (US)

(72) Inventors: I-Yeu Shen, Seattle, WA (US); John A. Sorensen, Seattle, WA (US); Naseeba Khouja, Seattle, WA (US); Wei Che Tai, Seattle, WA (US)

(73) Assignee: University of Washington, Seattle, WA (US)

( * ) Notice: Subject to any disclaimer, the term of this patent is extended or adjusted under 35 U.S.C. 154(b) by 1209 days.

(21) Appl. No.: 16/489,028

(22) PCT Filed: Mar. 12, 2018

(86) PCT No.: PCT/US2018/022069
§ 371 (c)(1),
(2) Date: Aug. 27, 2019

(87) PCT Pub. No.: WO2018/165674
PCT Pub. Date: Sep. 13, 2018

(65) Prior Publication Data
US 2020/0060612 A1     Feb. 27, 2020

Related U.S. Application Data

(60) Provisional application No. 62/469,854, filed on Mar. 10, 2017.

(51) Int. Cl.
*A61B 5/00*     (2006.01)
*A61B 5/11*     (2006.01)
(Continued)

(52) U.S. Cl.
CPC .......... *A61B 5/4851* (2013.01); *A61B 5/0051* (2013.01); *A61B 5/1111* (2013.01);
(Continued)

(58) Field of Classification Search
CPC ... A61B 5/4851; A61B 5/0051; A61B 5/1111; A61B 17/808; A61B 17/86;
(Continued)

(56) References Cited

U.S. PATENT DOCUMENTS

| 4,163,183 A | 7/1979 | Engelberger |
| 5,364,309 A | 11/1994 | Heidrich |

(Continued)

FOREIGN PATENT DOCUMENTS

| CN | 101965154 A | 2/2011 |
| CN | 102272795 A | 12/2011 |

(Continued)

OTHER PUBLICATIONS

Kaneko, "Relationship between the stiffness of the dental implant-bone system and the duration of the implant-tapping rod contact" Med Eng Phys. 16:310-315 (1994).
(Continued)

*Primary Examiner* — Eric F Winakur
*Assistant Examiner* — Abid A Mustansir
(74) *Attorney, Agent, or Firm* — McDonnell Boehnen Hulbert & Berghoff LLP

(57) ABSTRACT

An example method for detecting stability of a medical implant is provided. The method includes (a) applying a force to the medical implant with a probe, (b) based on the applied force, determining a response signal associated with a vibration of the medical implant, (c) comparing the determined response signal with a computer model of the medical implant, and (d) based on the comparison, determining an angular stiffness coefficient of the medical implant, wherein
(Continued)

the angular stiffness coefficient indicates a stability of the medical implant.

18 Claims, 26 Drawing Sheets

(51) Int. Cl.
    *A61B 17/80*     (2006.01)
    *A61B 17/86*     (2006.01)
    *A61B 90/00*     (2016.01)
    *A61C 5/70*     (2017.01)
    *A61C 8/00*     (2006.01)
    *A61C 19/04*     (2006.01)
    *A61F 2/32*     (2006.01)
    *A61F 2/38*     (2006.01)
    *A61F 2/46*     (2006.01)

(52) U.S. Cl.
    CPC ............ *A61B 17/808* (2013.01); *A61B 17/86* (2013.01); *A61C 5/70* (2017.02); *A61C 8/0089* (2013.01); *A61C 19/04* (2013.01); *A61F 2/32* (2013.01); *A61F 2/38* (2013.01); *A61F 2/468* (2013.01); *A61B 2090/066* (2016.02); *A61B 2562/0252* (2013.01); *A61F 2002/4667* (2013.01)

(58) Field of Classification Search
    CPC ...... A61B 2090/066; A61B 2562/0252; A61C 5/70; A61C 8/0089; A61C 19/04; A61C 8/00; A61F 2/32; A61F 2/38; A61F 2/468; A61F 2002/4667; A61F 2/4657
    See application file for complete search history.

(56) References Cited

U.S. PATENT DOCUMENTS

| | | | |
|---|---|---|---|
| 5,518,008 A | 5/1996 | Cucchiaro | |
| 6,203,437 B1 | 3/2001 | Durie | |
| 8,448,516 B2 | 5/2013 | Faulkner | |
| 9,949,644 B2 | 4/2018 | Li | |
| 10,806,352 B2 | 10/2020 | Sweeney | |
| 2002/0143268 A1* | 10/2002 | Meredith | A61B 5/1111 600/552 |
| 2004/0151214 A1 | 8/2004 | Syms | |
| 2005/0026113 A1 | 2/2005 | Chen et al. | |
| 2005/0134561 A1 | 6/2005 | Tierling | |
| 2007/0037123 A1* | 2/2007 | Mansueto | A61C 8/0022 433/173 |
| 2009/0030530 A1 | 1/2009 | Martin | |
| 2009/0092945 A1 | 4/2009 | Wu et al. | |
| 2009/0093887 A1 | 4/2009 | Walter | |
| 2009/0148811 A1 | 6/2009 | Pan | |
| 2009/0264754 A1 | 10/2009 | Dahl et al. | |
| 2011/0200965 A1 | 8/2011 | Petersson | |
| 2011/0259076 A1 | 10/2011 | Faulkner | |
| 2011/0311944 A1* | 12/2011 | Earthman | A61C 8/0089 433/119 |
| 2012/0046696 A1 | 2/2012 | Winslow | |
| 2013/0174639 A1 | 7/2013 | Earthman et al. | |
| 2015/0100067 A1 | 4/2015 | Cavanagh | |
| 2015/0177272 A1 | 6/2015 | Clark | |
| 2016/0204684 A1 | 7/2016 | Komatsu et al. | |
| 2016/0206201 A1 | 7/2016 | Li et al. | |
| 2016/0338751 A1 | 11/2016 | Kellar | |
| 2016/0356745 A9 | 12/2016 | Faulkner et al. | |
| 2017/0020437 A1 | 1/2017 | Nielsen | |
| 2020/0060612 A1 | 2/2020 | Shen | |

FOREIGN PATENT DOCUMENTS

| | | |
|---|---|---|
| CN | 104268359 A | 1/2015 |
| CN | 104281759 A | 1/2015 |
| CN | 104361164 A | 2/2015 |
| CN | 104684841 A | 6/2015 |
| CN | 106021876 A | 10/2016 |
| EP | 0687163 B1 | 8/2000 |
| EP | 1641394 B1 | 6/2004 |
| JP | 1996089517 | 4/1996 |
| JP | 1998505519 | 6/1998 |
| KR | 20060067926 A | 6/2006 |
| WO | WO 2016/204684 | 12/2016 |

OTHER PUBLICATIONS

Khouja—Dissertation: "In Search of An Improved Methodology for Measuring Dental Implant Stability: Combining Experimental Model Analysis (EMA) and Finite Element Analysis (FEA) to Achieve Maximum Reliability" University of Washington (2017).

Khouja et al, "A Critique of Resonance Frequency Analysis and a Novel Method for Quantifying Dental Implant Stability in vitro", Int J Oral Maxillofac Implants 34:595-603 (2019).

Kielbassa et al., "Randomized controlled trial comparing a variable-thread novel tapered and a standard tapered implant: Interim one-year results", J Prosthet Dent 101: 293-305 (2009).

Kim et al, "Resonance frequency analysis as a predictor of early implant failure in the partially edentulous posterior maxilla following immediate nonfunctional loading or delayed loading with single unit restorations", Clin. Oral Impl. Res. 26 183-190 (2015).

Krafft et al, "Osstell Resonance Frequency Measurement Values as a Prognostic Factor in Implant Dentistry", J Oral Implantol 41:e133-137 (2015).

Lachmann et al, "Resonance frequency analysis and damping capacity assessment. Part 2: peri-implant bone loss follow-up. An in vitro study with the Periotest and Osstell instruments", Clin Oral Implants Res 17:80-84 (2006).

LaMalfa-Ribolla et al, "Modeling the electromechanical inpedance technique for the assessment of dental implant stability", Journal Biomechanics vol. 48/Issue 10: 1713-1720.

LaMalfa-Ribolla et al, "On the use of the electromechanical impedance technique for the assessment of dental implant stability: Modeling and experimentation", Journal of Intelligent Material Systems and Structures vol. 26/Issue 16: 2266-2280.

Lang et al, "A systematic review on survival and success rates of implants placed immediately into fresh extraction sockets after at least 1 year", Clin Oral Implants Res. Suppl 5:39-66 (2012).

Lekholm et al, Chapter 12—"Patient selection and preparation" Tissue integrated prostheses: Osseointegration in clinical dentistry, 199-209. Chicago: Quintessence Publishing Co. Inc (1985).

Linder et al, "Electron microscopic analysis of the bone-titanium interface", Acta Orthop Scand 54:45-52 (1983).

Lukas et al, "Periotest—a dynamic procedure for the diagnosis of the human periodontium", Clin Phys Physiol Meas 11:65-75 (1990).

Manresa et al, "The comparison between implant stability quotient and bone-implant contact revisited: an experiment in Beagle dog", Clin. Oral Impl. Res. 25 1213-1221 (2014).

Marquezan et al, ", Does bone mineral density influence the primary stability of dental implants? A systematic review", Clin. Oral Impl. Res. 23 767-774 (2012).

Martinez et al, "Optimal implant stabilization in low density bone", Clin Oral Implants Res 12:423-432 (2001).

Meredith et al, "Assessment of implant stability as a prognostic determinant", Int J Prosthodont 11:491-501 (1998).

Meredith et al, "Quantitative determination of the stability of the implant-tissue interface using resonance frequency analysis", Clin Oral Implants Res 7:261-267 (1996).

Meredith et al, "Relationship between contact time measurements and PTV values when using the Periotest to measure implant stability", Int J Prosthodont 11:269-275 (1998).

Miyamoto et al, "Influence of cortical bone thickness and implant length on implant stability at the time of surgery—clinical, prospective, biomechanical, and imaging study", Bone 37:776-780 (2005).

Monje et al, "A systematic review on marginal bone loss around short dental implants (<10 mm) for implant-supported fixed prostheses", Clin Oral Implants Res. 25:1119-1124 (2014).

(56) References Cited

OTHER PUBLICATIONS

Moriwaki et al, "Influence of Implant Length and Diameter, Bicortical Anchorage, and Sinus Augmentation on Bone Stress Distribution: Three-Dimensional Finite Element Analysis", Int J Oral Maxillofac Implants 31:e84-e91 (2016).
Nedir et al, "Predicting osseointegration by means of implant primary stability", Clin Oral Implants Res 15:520-528 (2004).
Norton et al, "Bone classification: an objective scale of bone density using the computerized tomography scan", Clin Oral Implants Res 12:79-84 (2001).
Ostman et al, "Resonance frequency analysis measurements of implants at placement surgery", Int J Prosthodont 19:77-83; discussion 84 (2006).
O'Sullilvan et al, "Measurements comparing the initial stability of five designs of dental implants: A human cadaver study", Clin Implant Dent Relat Res 2: 85-92 (2000).
Salvi et al, ". Diagnostic parameters for monitoring peri-implant conditions" Int J Oral Maxillofac Implants 19 Suppl: 116-127 (2004).
Sennerby et al, "Two different implant designs and impact of related drilling protocols on primary stability in different bone densities: an in vitro comparison study", Int J Oral Maxillofac Implants 30:564-568 (2015).
Shiffler et al, "Effect of length, diameter, intraoral location on implant stability", Oral Surg Oral Med Oral Pathol Oral Radiol 122: e193-e198 (2016).
Swain et al, ". A dynamic analytical model for impact evaluation of percutaneous implants", J Biomech Eng 130:051013 (2008).
Swami et al, "Current trends to measure implant stability", J Indian Prosthodont Soc 16: 124-130 (2016).
Tabassum et al, "Influence of surgical technique and surface roughness on the primary stability of an implant in artificial bone with different cortical thickness: A laboratory study", Clin Oral Implants Res 21: 213-220 (2010).
Tang et al, "Torsional resonance frequency analysis: a novel method for assessment of dental implant stability", Clin. Oral Impl. Res. 26 615-622 (2015).
Toniollo et al, "Finite Element Analysis of Bone Stress in the Posterior Mandible Using Regular and Short Implants, in the Same Context, with Splinted and Nonsplinted Prostheses", Int J Oral Maxillofac Implants 32:e199-e206 (2017).
Tsay et al, "Free Vibration Analysis of PZT Glide Heads", ASME Journal of Tribology, vol. 121, pp. 984-988.
Tsolaki et al, "Comparison of osteotome and conventional drilling techniques for primary implant stability: an in vitro study", J Oral Implantol (2016).
Turkyilmaz et al, "Influence of bone density on implant stability parameters and implant success: a retrospective clinical study", BMC Oral Health 8:32 (2008).
"Turkyilmaz et al, ""Two Alternative Surgical Techniques for Enhancing Primary Implant Stability in thePosterior Maxilla: A Clinical Study Including Bone Density, Insertion Torque, and Resonance Frequency Analysis Data"" Clinical Implant Dentistry and Related Research vol. 10, No. 4, (2008)".
Van Steenberghe et al, "Damping characteristics of bone-to-implant interfaces. A clinical study with the Periotest device", Clin Oral Implants Res 6:31-39 (1995).
Vina-Almunia et al, "Survival of implants placed with the osteotome technique: an update" Med Oral Patol Oral Cir Bucal 17:e765-768 (2012).
Westover et al, "Advanced system for implant stability testing (asist)", J Biomech 49: 3651-3659 (2016).
Winkler et al, "Implant survival to 36 months as related to length and diameter", Ann Periodontol 5:22-31 (2000).
Winkler et al, "Stability of implants and natural teeth as determined by the periotest over 60 months of function", J Oral Implantol 27: 198-203 (2001).
Yamaguchi et al "Development and application of a direct method to observe the implant/bone interface using simulated bone", Springerplus 5: 494 (2016).

Yamaguchi et al "Effect of implant design on primary stability using torque-time curves in artificial bone", Int J Implant Dent 1: 21 (2015).
Jennings et al., "The measurement of muscle stiffness in anterior cruciate injuries—an experiment revisited", Clinical Biomechanics, vol. 13, No. 2 pp. 138-140 (1998).
Schmidt et al., "Which axial and bending stiffnesses of posterior implants are required to design a flexible lumbar stabilization systems?" Journal of Biomechanics, vol. 42, No. 1, pp. 48-54 (2009).
European Search Report for corresponding European application No. 18763599.0, dated Oct. 30, 2020.
Schroeder et al, "[tissue reaction to an implant of a titanium hollow cylinder with a titanium surface spray layer]", SSO Schweiz Monatsschr Zahnheilkd 86: 713-727 (1976) English summary on p. 726.
The International Search Report (ISR) with Written Opinion for PCT/US2018/022069 dated May 30, 2018, pp. 1-9.
Hansson et al., "The implant thread as a retention element in cortical bone: the effect of thread size and thread profile: a finite element study", Journal of Biomechanics 36:1247-1258 (2003).
Schmidt et al., "Which axial and bening stiffnesses of posterior implants are required to design a flexible lumbar stabilization system?", Journal of Biomechanics, 42:48-54 (2009).
Jennings et al., "Brief report—The measurement of muscle stiffness in anterior cruciate injuries—an experiment revisited", Clinical Biomechanics, 13(2):138-140 (1998).
Hongqing, "Research on the Synergetic Damping Mechanism of the Biological Structures and Design Method of the the Bionic Vibration Damping Devices", Chinese language (2014.
Abbas et al, "Evaluation of Stress Distribution on Implant-Retained Auricular Prostheses: The finite Element Method" Int J Oral Maxillofac Implants 32:251-258 (2017).
Abuhussein et al, "The effect of thread pattern upon implant osseointegration", Clin Oral Implants Res 21: 129-136 (2010).
Ahmad et al "Assessment of the primary stability of dental implants in artificial bone using resonance frequency and percussion analyses", Int J Oral Maxillofac Implants 28:89-95 (2013).
Ahn et al, "Differences in implant stability associated with various methods of preparation of the implant bed: an in vitro study" J Prosthet Dent 107:366-372 (2012).
Ai-Nawas et al, "Insertion torque and resonance frequency analysis of dental implant systems in an animal model with loaded implants", Int J Oral Maxillofac Implants 21: 726-732 (2006).
Andersen et al, "Immediate loading of single-tooth ITI implants in the anterior maxilla: a prospective 5-year pilot study", Clin Oral Implants Res. 13:281-287 (2002).
Aparicio et al, "Validity and clinical significance of biomechanical testing of implant/bone interface", Clin Oral Implants Res 17 Suppl 2: 2-7 (2006).
Atsumi et al, "Methods used to assess implant stability: Current status", Int J Oral Maxillofac Implants 22(5): 743-754 (2007).
Barikani et al, "The Effect of Implant Length and Diameter on the Primary Stability in Different Bone Types" Journal of Dentistry (Tehran, Iran) 10:449-455 (2013).
Barikani et al, The effect of shape, length and diameter of implants on primary stability based on resonance frequency analysis. Dental Research Journal 2014;11:87-91.
Bilhan et al, "Comparison of the Primary Stability of Two Implant Designs in Two Different Bone Types: An In Vitro Study" Int J Oral Maxillofac Implants 30:1036-1040 (2015).
Boemio et al, "Assessment of dental implant stability by means of the electromechanical impedance method", Smart Materials and Structures 20:045008 (11 pages) (2011).
Branemark et al, "Osseointegrated implants in the treatment of the edentulous jaw. Experience from a 10-year period", Scand J Plast Reconstr Surg Suppl 16: 1-132 (1977).
Branemark et al, "Osseointegration and its experimental background", J Prosthet Dent 50:399-410 (1983).
Branemark et al, "Tissue-integrated prostheses: Osseointegration in Clinical Dentistry" Chicago; London: Quintessence Publishing., Ed. Per-ingvar Branemark, George A. Zarb, and Tomas Albrektsson; pp. 1-36 (1985).

(56) References Cited

OTHER PUBLICATIONS

Brunski et al, "The influence of functional use of endosseous dental implants on the tissue-implant interface" I. Histological aspects. J Dent Res. 58:1953-1969 (1979).
Buser et al, "Modern implant dentistry based on osseointegration: 50 years of progress, current trends and open questions", Periodontol 2000 73: 7-21 (2017).
Cavallaro et al, "Clinical methodologies for achieving primary dental implant stability: the effects of alveolar bone density" J Am Dent Assoc 140:1366-1372 (2009).
Chan et al, "Implant primary stability determined by resonance frequency analysis in surgically created defects: a pilot cadaver study", Implant Dent 19:509-519 (2009).
Chrcanovic et al, "A. Reasons for failures of oral implants", J Oral Rehabil. 41:443-476 (2014).
Cooper, "Factors influencing primary dental implant stability remain unclear", J Evid Based Dent Pract 12:185-186 (2012).
De Freitas et al, "Mandibular implant-supported removable partial denture with distal extension: a systematic review", J Oral Rehabil 39:791-798 (2012).
Degidi et al, "Influence of Underpreparation on Primary Stability of Implants Inserted in Poor Quality Bone Sites: An In Vitro Study", Journal of Oral and Maxillofacial Surgery 73:1084-1088 (2015).
Derhami et al, "Assessment of the periotest device in baseline mobility measurements of craniofacial implants", Int J Oral Maxillofac Implants 10:221-229 (1995).
Dinh et al, "Analysis of percussion response of dental implants: an in vitro study" Mater Sci Eng C Mater Biol Appl. 33:2657-2663 (2003).
Elias et al, "Influence of implant shape, surface morphology, surgical technique and bone quality on the primary stability of dental implants", J Mech Behav Biomed Mater 16: 169-180 (2012).
Engelhardt et al, "Annual failure rates and marginal bone-level changes of immediate compared to conventional loading of dental implants. A systematic review of the literature and meta-analysis", Clin Oral Implants Res. 26:671-687 (2015).
Ersani et al,"Resonance frequency analysis of one-stage dental implant stability during the osseointegration period", J Periodontol 76:1066-1071 (2005).
Esposito et al, "Interventions for replacing missing teeth: different times for loading dental implants", . Cochrane Database Syst Rev. CD003878 (2013).
Esposito et al, "Interventions for replacing missing teeth: Different types of dental implants", Cochrane Database Syst Rev: CD003815 (2014).
Esposito et al, "Interventions for replacing missing teeth: management of soft tissues for dental implants", Cochrane Database Syst Rev. CD006697 (2007).
Farre-Pages et al, "Relation between bone density and primary implant stability", Med Oral Patol Oral Cir Bucal. Jan. 1;16 (1):e62-7 (2011).
Faulkner et al, "The use and abuse of the Periotest for 2-piece implant/abutment systems" Int J Oral Maxillofac Implants 16:486-494 (2001).
Ferrigno et al, "A long-term follow-up study of non-submerged ITI implants in the treatment of totally edentulous jaws Part I: Ten-year life table analysis of a prospective multicenter study with 1286 implants", Clin Oral Implants Res 13:260-273 (2002).
Friberg et al, "Stability measurements of one-stage Branemark implants during healing in mandibles. A clinical resonance frequency analysis study", Int J Oral Maxillofac Surg 28:266-272 (1999).
Fu et al, "Correlation Between Resonance Frequency Analysis and Bone Quality Assessments at Dental Implant Recipient Sites", Int J Oral Maxillofac Implants 32:1890-187 (2017).
Gomez-Polo et al, "Does Length, Diameter, or Bone Quality Affect Primary and Secondary Stability in Self-Tapping Dental Implants?", J Oral Maxillofac Surg (2016).

Haiat et al, "Effects of biomechanical properties of the bone-implant interface on dental implant stability: from in silico approaches to the patient's mouth", Annu Rev Biomed Eng 16:187-213 (2014).
Hobkirk et al, "Biomechanical aspects of oral implants", Consensus report of working group 1. Clin Oral Implants Res 17 Suppl 2: 52-54 (2006).
Hsu et al, "The effects of cortical bone thickness and trabecular bone strength on noninvasive measures of the implant primary stability using synthetic bone models", Clin Implant Dent Relat Res 15:251-261 (2013).
Huang et al, "Resonance frequency assessment of dental implant stability with various bone qualities: a numerical approach", Clin Oral Implants Res 13:65-74 (2002).
Huang et al, "Assessing the implant/bone interface by using natural frequency analysis", Oral Surg Oral Med Oral Pathol Oral Radiol Endod 90:285-291 (2000).
Huang et al, "Early detection of implant healing process using resonance frequency analysis", Clin Oral Implants Res 14:437-443 (2003).
Huang et al, "Factors influencing the resonance frequency of dental implants", J Oral Maxillofac Surg 61:1184-1188 (2003).
Ioannidou et al, "Does loading time affect implant survival? A meta-analysis of 1,266 implants", J Periodontol 76:1252-1258 (2005).
Iso, "Accuracy (trueness and precision) of measurement methods and results—Part 1: General principles and definitions" pp. 1-26 (1998).
Javed et al, "Role of primary stability for successful osseointegration of dental implants: Factors of influence and evaluation", Interventional Medicine and Applied Science 5:162-167 (2013).
Javed et al, "The Role of primary stability for successful immediate loading of dental implants. A literature review", Journal of Dentistry 38:612-20 (2010).
Jensen, "Dental extraction, immediate placement of dental implants, and immediate function", Oral Maxillofac Surg Clin North Am. 27:273-282 (2015).
Jeong et al, "Consideration of various bone quality evaluation methods", Implant Dent 22:55-59 (2013).
Argatov et al., "A Simple Mathematical Model for the Resonance Frequency Analysis of Dental Implant Stability: Implant Clamping Quotient":, Mechanical Research Communication, 95:67-70 (Dec. 20, 2018).
Zhai et al., "Effects on the TGorsional Vibration Behavior in the Investigation of Dental Implant Osseointegration using Resonance Frequency Analysis: A Numerical Approach", Medical & Biological Engineering & Computing, 55:1649-1658 (Feb. 7, 2017).
Korabi et al., "On Stress/Strain Shielding and the Material Stiffness Paradigm for Dental Implants", Clinical Implant Dentistry, 19(5):935-943 (Jun. 13, 2017).
Xu, Weiwei et al.—A Vibratory, Subresonant Diagnostic Device to Measure Dental Implant Stability Via Angular Stiffness. J. Med. Devices. Sep. 2021, 15(3): 031015. Published Aug. 2, 2021.
Elias, J.J. et al.—A Dynamic Modal Testing Technique for Noninvasive Assessment of Bone-Dental Implant Interfaces. Int J Oral Maxillofac Implants. Nov.-Dec. 1996;11(6):728-34. PMID: 8990633. Published 1996.
Liu, Y. et al.—Challenges of Using Resonance Frequency Analysis to Identify Stability of a Dental Implant Placed in the Mandible. Liu Y, Sorensen JA, Shen IY. Challenges of Using Resonance Frequency Analysis to Identify Stability of a Dental Implant Placed in the Mandible. Int J Oral Maxillofac Implants. Mar.-Apr. 2021;36(2):e7-e21. doi: 10.11607/jomi.8579. PMID: 33909715. Published Mar. 1, 2021.
Lannocca, M. et al.—Intra-Operative Evaluation of Cementless Hip Implant Stability: A Prototype Device based on Vibration Analysis. Medical Engineering & Physics, vol. 29(8), p. 886-894. Published Nov. 13, 2006.
Tang, Y. et al.—Torsional Resonance Frequency Analysis: A Novel Method for Assessment of Dental Implant Stability. Clinical Oral Implants Research, 26, 2015, 615-622. Published Feb. 25, 2014.
Chen MHM, Lyons K, Tawse-Smith A, Ma S. Resonance frequency analysis in assessing implant stability: a retrospective analysis. International Journal of Prosthodontics 2019;32: 317-326.

(56) References Cited

OTHER PUBLICATIONS

Chen MHM, Lyons K, Tawse-Smith A, Ma S. Clinical significance of the use of resonance frequency analysis in assessing implant stability: a systematic review. International Journal of Prosthodontics 2019;32: 51-58.

Andersson P, Pagliani L, Verrocchi D, Volpe S, Sahlin H, Sennerby L. Factors influencing resonance frequency analysis (RFA) measurements and 5-year survival of neoss dental implants. International Journal of Dentistry 2019; 2019: Article ID 3209872.

Baftijari D, Benedetti, Kirkov A, Iliev A, Stamatoski A, Baftijari F, Deliverska EG, Gjorgievska E. Assessment of primary and secondary implant stability by resonance frequency analysis in anterior and posterior segments of maxillary edentulous ridges. Journal of IMAB 2018;24: 2058-2064.

Yao CJ, Ma L, Mattheos N. Can resonance frequency analysis detect narrow marginal bone defects around dental implants? An ex vivo animal pilot study. Australian Dental Journal 2018;62:433-439.

Kumar VV, Kumar U, Pillai V, Ponnusamy V, Al-Nawas B, Kuriakose MA. Implant stability and bone characteristics in free fibula flaps used for jaw reconstruction: a prospective cohort study. Int J Oral Maxillofac Implants 2017;32: 1145-1152.

Fu MW, Fu E, Lin FG, Chang WJ, Hsieh YD, Shen EC. Correlation between resonance frequency analysis and bone quality assessments at dental implant recipient sites. Int J Oral Maxillofac Implants 2017;32:180-187.

Monje A, Ortega-Oller I, Galindo-Moreno P, Catena A, Monje F, O'Valle F, Suarez F, Wang HL. Sensitivity of resonance frequency analysis for detecting early implant failure: a case-control study. Int J Oral Maxillofac Implants 2014;29:456-461.

Kim SJ, Ribeiro ALVL, Atlas AM, Saleh N, Royal J, Radvar M, Korostoff J. Resonance frequency analysis as a predictor of early implant failure in the partially edentulous posterior maxilla following immediate nonfunctional loading or delayed loading with single unit restorations. Clin Oral Impl Res 2015; 26:183-190.

Manresa C, Bosch M, Echeverría JJ. The comparison between implant stability quotient and bone-implant contact revisited: an experiment in Beagle dog. Clin Oral Impl Res 2014; 25:1213-1221. 20.

Vayron R, Nguyen VH, Lecuelle B, Haiat G. Evaluation of dental implant stability in bone phantoms: Comparison between a quantitative ultrasound technique and resonance frequency analysis. Clinical Implant Dentistry and Related Research 2018;20: 470-478.

Vayron R, Nguyen VH, Lecuelle B, Lomami HA, Meningaud JP, Bosc R, Haiat G., Comparison of resonance frequency analysis and of quantitative ultrasound to assess dental implant osseointegration. Sensors 2018;18:1397.

Lages FS, Douglas-de Oliveira DW, Costa FO. Relationship between implant stability measurements obtained by insertion torque and resonance frequency analysis: A systematic review. Clinical Implant Dentistry and Related Research 2018;20:26-33.

Westover L, Faulkner G, Hodgetts W, Raboud D. Advanced System for Implant Stability Testing (ASIST). J Biomech 2016;25:3651-3659.

Lukas D, Schulte W. Periotest—a dynamic procedure for the diagnosis of the human periodontium. Clin Phys Physiol Meas 1990;11:65-75.

Winkler S, Morris HF, Spray JR. Stability of implants and natural teeth as determined by the Periotest over 60 months of function. J Oral Implantol 2001;27:198-203.

Swain R, Faulkner G, Raboud D, Wolfaardt J. A dynamic analytical model for impact evaluation of percutaneous implants. J Biomech Eng 2008;130:051013.

Khouja N, Tai WC, Shen IY, Sorensen JA. A critique of resonance frequency analysis and a novel method for quantifying dental implant stability in vitro. Int J Oral Maxillofac Implants 2019;34: 595-603.

* cited by examiner

METHODS AND SYSTEMS TO MEASURE AND EVALUATE STABILITY OF MEDICAL IMPLANTS

CROSS-REFERENCE TO RELATED APPLICATIONS

This application is a U.S. national phase of International Application No. PCT/US2018/022069, filed on Mar. 12, 2018, which claims priority to U.S. Provisional Application No. 62/469,854, filed Mar. 10, 2017, both of which are incorporated by reference herein in their entirety.

BACKGROUND

Unless otherwise indicated herein, the materials described in this section are not prior art to the claims in this application and are not admitted to be prior art by inclusion in this section.

Medical implants are commonly used in a variety of medical procedures. One medical implant that is particularly common is dental implants. Dental implants are widely used for tooth replacement and are considered the treatment of choice for reliability, longevity and conservation of tooth structure. The number of dental implants placed has grown significantly over the past decade. According to the American Academy of Implant Dentistry, an estimated 500,000 dental implants are placed each year and approximately 3 million individuals have dental implants in the U.S. alone. Primary stability is a significant factor in successful dental implant treatment. Primary stability is created by the mechanical interlocking of the implant into the surrounding bone structure. Secondary stability is the direct structural, functional and biologic bonding between ordered living bone cells and the implant, known as osseointegration. Achieving sufficient primary stability is an important factor leading to effective secondary stability.

As a critical indicator of implant health evaluation of dental implant stability has proven one of the most challenging procedures for clinicians. A great amount of research on dental implant stability has been performed yet no criteria are available for measurement standards. Radiographs are the most commonly used method of clinical evaluation of implants, but they are normally two-dimensional and only provide partial representation of the implant status. Another common and simple technique is the percussion method whereby clinicians merely tap on the implant with a metallic instrument. A dull thud sound indicates a potentially compromised implant. This technique is highly subjective.

Consequently, there is great clinical need for a non-invasive device with a high level of sensitivity capable of detecting small changes in dental implant stability. A device proficient at measuring smaller changes in implant stability would be helpful in many ways, including: evaluation at different stages of healing towards successful osseointegration, aid critical diagnosis and treatment planning, facilitate the decision process as to when an implant should be loaded and for monitoring implant status at recall visits.

Some current non-invasive devices used for assessing implant stability are based on measurement of the resonance frequency of the implant-bone system. First, these devices do not measure the stiffness at the implant-bone interface, which is what determines implant stability. Second, these tests are often performed with the implant connected to an abutment or the testing instrument. These connected components can significantly affect the measured frequency of the bone-implant system. Third, the measurement data can be scattered and inconclusive for reasons such as material property variations, insufficient joining of parts with abutment screw, or boundary conditions. As such, improved methods and systems to measure and evaluate the stability of medical implants that address the issues outlined above would be desirable.

SUMMARY

Example methods and systems to measure and evaluate the stability of medical implants are described herein. In a first aspect, a method for detecting stability of a medical implant is provided. The method includes (a) applying a force to the medical implant with a probe, (b) based on the applied force, determining a response signal associated with a vibration of the medical implant, (c) comparing the determined response signal with a computer model of the medical implant, and (d) based on the comparison, determining an angular stiffness coefficient of the medical implant, wherein the angular stiffness coefficient indicates a stability of the medical implant.

In a second aspect, a system for detecting stability of a medical implant is provided. The system includes (a) a probe configured to detect a response signal associated with a vibration of the medical implant in response to a force applied to the medical implant, and (b) a computing device in communication with the probe. The computing device is configured to (i) compare the determined response signal with a computer model of the medical implant, and (ii) based on the comparison, determine an angular stiffness coefficient of the medical implant, wherein the angular stiffness coefficient indicates a stability of the medical implant.

In a third aspect, a non-transitory computer-readable medium having stored thereon instructions that, when executed by one or more processors of a computing device, cause the computing device to perform functions. The functions include (a) applying a force to the medical implant, (b) based on the applied force, determining a response signal associated with a vibration of the medical implant, (c) comparing the determined response signal with a computer model of the medical implant, and (d) based on the comparison, determining an angular stiffness coefficient of the medical implant, wherein the angular stiffness coefficient indicates a stability of the medical implant.

These as well as other aspects, advantages, and alternatives, will become apparent to those of ordinary skill in the art by reading the following detailed description, with reference where appropriate to the accompanying drawings.

DETAILED DESCRIPTION

Figure 1:
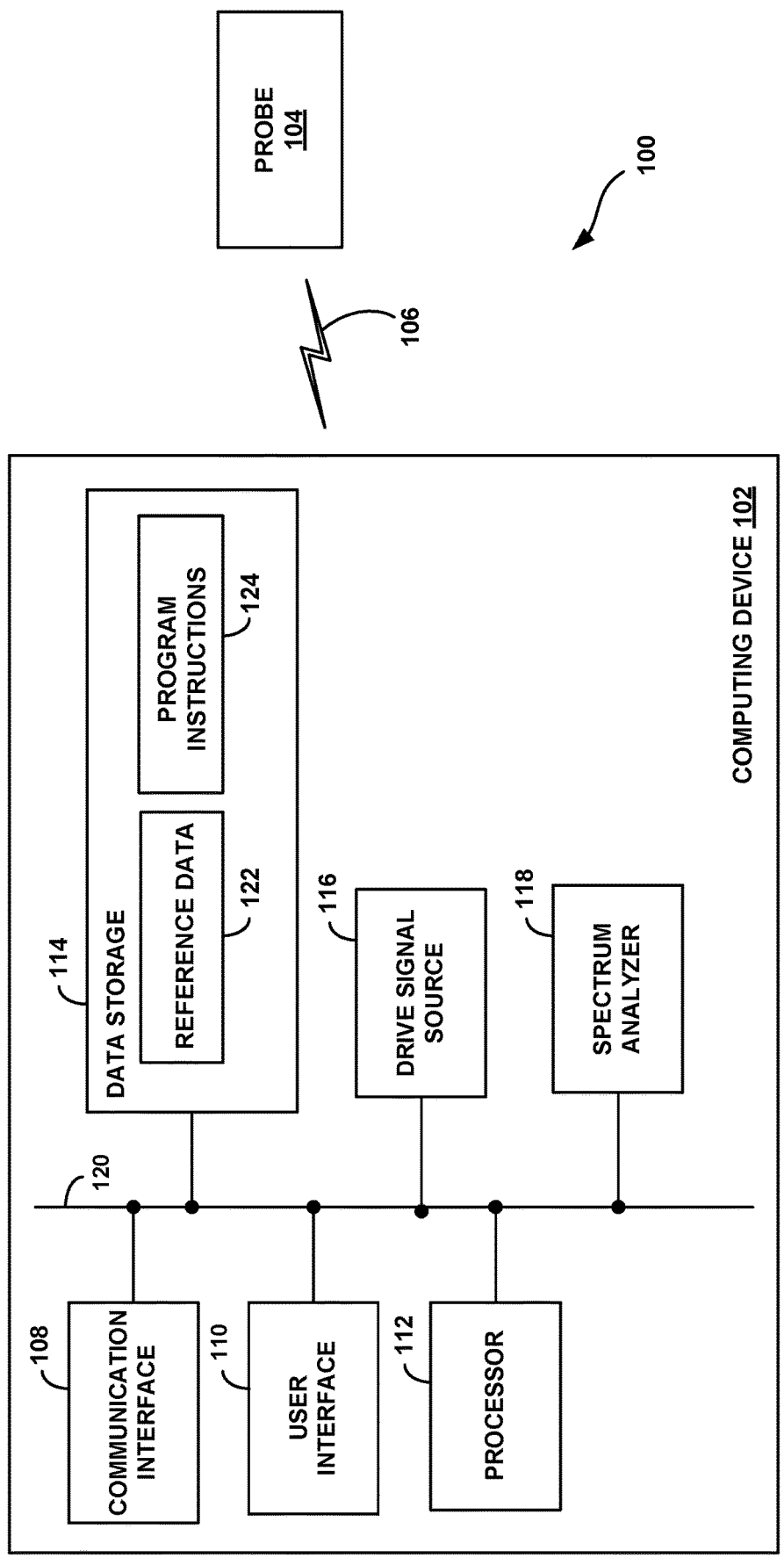
FIG. 1 is a simplified block diagram of a system, according to an example embodiment.

Example methods and systems are described herein. It should be understood that the words "example" and "exemplary" are used herein to mean "serving as an example, instance, or illustration." Any embodiment or feature described herein as being an "example" or "exemplary" is not necessarily to be construed as preferred or advantageous over other embodiments or features. In the following detailed description, reference is made to the accompanying figures, which form a part thereof. In the figures, similar symbols typically identify similar components, unless context dictates otherwise. Other embodiments may be utilized, and other changes may be made, without departing from the scope of the subject matter presented herein.

The example embodiments described herein are not meant to be limiting. It will be readily understood that the aspects of the present disclosure, as generally described herein, and illustrated in the figures, can be arranged, substituted, combined, separated, and designed in a wide variety of different configurations, all of which are explicitly contemplated herein.

As used herein, with respect to measurements, "about" means+/−5%.

As used herein, "medical implant" means a dental implant, a dental crown, a dental restoration, a bone screw, a plate, a hip implant, or a knee implant, as non-limiting examples.

Unless otherwise indicated, the terms "first," "second," etc. are used herein merely as labels, and are not intended to impose ordinal, positional, or hierarchical requirements on the items to which these terms refer. Moreover, reference to, e.g., a "second" item does not require or preclude the existence of, e.g., a "first" or lower-numbered item, and/or, e.g., a "third" or higher-numbered item.

Reference herein to "one embodiment" or "one example" means that one or more feature, structure, or characteristic described in connection with the example is included in at least one implementation. The phrases "one embodiment" or "one example" in various places in the specification may or may not be referring to the same example.

As used herein, a system, apparatus, device, structure, article, element, component, or hardware "configured to" perform a specified function is indeed capable of performing the specified function without any alteration, rather than merely having potential to perform the specified function after further modification. In other words, the system, apparatus, structure, article, element, component, or hardware "configured to" perform a specified function is specifically selected, created, implemented, utilized, programmed, and/or designed for the purpose of performing the specified function. As used herein, "configured to" denotes existing characteristics of a system, apparatus, structure, article, element, component, or hardware, which enable the system, apparatus, structure, article, element, component, or hardware to perform the specified function without further modification. For purposes of this disclosure, a system, apparatus, structure, article, element, component, or hardware described as being "configured to" perform a particular function may additionally or alternatively be described as being "adapted to" and/or as being "operative to" perform that function.

In the following description, numerous specific details are set forth to provide a thorough understanding of the disclosed concepts, which may be practiced without some or all of these particulars. In other instances, details of known devices and/or processes have been omitted to avoid unnecessarily obscuring the disclosure. While some concepts will be described in conjunction with specific examples, it will be understood that these examples are not intended to be limiting.

A. OVERVIEW

Example embodiments of the present disclosure include methods and devices to measure dynamic properties of a medical implant. In many embodiments, the devices are electromechanical (EM) devices. The dynamic properties include natural frequencies, linear stiffness, and angular stiffness. High values of these quantities are indicative of the stability of medical implants, such as dental implants. However, these quantities may be difficult to measure accurately and precisely. For example, natural frequencies and linear stiffness may change significantly due to the presence of abutment or measurement locations. As a result, they may not serve as good indicators of implant stability. Similarly, angular stiffness may be difficult to measure directly with existing technology. Moreover, existing devices measure natural frequencies of medical implants require disassembly of the entire restoration/abutment/implant complex. This is often a task that cannot be achieved.

In response to these needs, embodiments of the present disclosure involve device(s) that measure angular stiffness directly, and/or method(s) that could extract angular stiffness from measured natural frequencies or linear stiffness via a computer model. In particular, embodiments of the present disclosure provide a probe in combination with a finite element simulation of a medical implant. A computing device can include a database of finite element simulations of various implants that are commercially available. The probe can apply a force to the medical implant to thereby determine a response signal associated with a vibration of the medical implant. The determined response signal may then be compared to the finite element simulation of the medical implant. Based on the comparison, an angular stiffness coefficient of the medical implant may be determined. The angular stiffness coefficient indicates a stability of the medical implant. In particular, a high value for the angular stiffness coefficient may represent a stable implant, while a low angular stiffness coefficient value may represent an unstable or unsecure implant.

It should be understood that the above examples of the method are provided for illustrative purposes, and should not be construed as limiting.

B. EXAMPLE SYSTEM

FIG. 1 is a simplified block diagram of a system 100, according to an example embodiment. Such a system 100 may be used by a medical professional to detect the stability of a medical implant in a patient. The system includes a computing device 102 and a probe 104. The probe 104 may be used to apply a mechanical force or displacement to a surface of a medical implant or bone within which the medical implant is implanted. The probe 104 may be configured to deliver a mechanical force, for example, via one or more piezoelectric transducers, toward a distal end of the probe 104, for example, for detecting properties of an area or region of a medical implant disposed proximate to the distal end of probe 104. In addition, the probe 104 may be configured to detect, for example, via one or more optical or piezoelectric sensors, mechanical movement for further processing. The probe 104 may be configured to detect a response signal associated with a vibration of the medical implant in response to a force applied to the medical implant. Additional details of the probe 104 are discussed below in relation to FIGS. 22-27.

The probe 104 may be communicatively coupled to the computing device 102. In an example embodiment, computing device 102 communicates with the probe 104 using a communication link 106 (e.g., a wired or wireless connection). The probe 104 and the computing device 102 may contain hardware to enable the communication link 106, such as processors, transmitters, receivers, antennas, etc. The computing device 102 may be any type of device that can receive data and display information corresponding to or associated with the data. By way of example and without limitation, computing device 102 may be a cellular mobile telephone (e.g., a smartphone), a computer (such as a desktop, laptop, notebook, tablet, or handheld computer), a personal digital assistant (PDA), a home automation component, a digital video recorder (DVR), a digital television, a remote control, a wearable computing device, or some other type of device. It should be understood that the computing device 102 and the probe 104 may be provided in the same physical housing, or the computing device 102 and the probe 104 may be separate components that communicate with each other over a wired or wireless communication link 106.

In FIG. 1, the communication link 106 is illustrated as a wireless connection; however, wired connections may also be used. For example, the communication link 106 may be a wired serial bus such as a universal serial bus or a parallel bus. A wired connection may be a proprietary connection as well. The communication link 106 may also be a wireless connection using, e.g., BLUETOOTH radio technology, BLUETOOTH LOW ENERGY (BLE), communication protocols described in IEEE 802.11 (including any IEEE 802.11 revisions), Cellular technology (such as GSM, CDMA, UMTS, EV-DO, WiMAX, or LTE), or ZIGBEE technology, among other possibilities. The probe 104 may be accessible via the Internet.

As shown in FIG. 1, computing device 102 may include a communication interface 108, a user interface 110, a processor 112, data storage 114, a drive signal source 116, and a spectrum analyzer 118, all of which may be communicatively linked together by a system bus, network, or other connection mechanism 120.

Communication interface 108 may function to allow computing device 102 to communicate, using analog or digital modulation, with other devices, access networks, and/or transport networks. Thus, communication interface 108 may facilitate circuit-switched and/or packet-switched communication, such as plain old telephone service (POTS) communication and/or Internet protocol (IP) or other packetized communication. For instance, communication interface 108 may include a chipset and antenna arranged for wireless communication with a radio access network or an access point. Also, communication interface 108 may take the form of or include a wireline interface, such as an Ethernet, Universal Serial Bus (USB), or High-Definition Multimedia Interface (HDMI) port. Communication interface 108 may also take the form of or include a wireless interface, such as a Wifi, global positioning system (GPS), or wide-area wireless interface (e.g., WiMAX or 3GPP Long-Term Evolution (LTE)). However, other forms of physical layer interfaces and other types of standard or proprietary communication protocols may be used over communication interface 108. Furthermore, communication interface 108 may comprise multiple physical communication interfaces (e.g., a Wifi interface, a short range wireless interface, and a wide-area wireless interface).

User interface 110 may function to allow computing device 102 to interact with a human or non-human user, such as to receive input from a user and to provide output to the user. Thus, user interface 110 may include input components such as a keypad, keyboard, touch-sensitive or presence-sensitive panel, computer mouse, trackball, joystick, microphone, and so on. User interface 110 may also include one or more output components such as a display screen which, for example, may be combined with a presence-sensitive panel. The display screen may be based on CRT, LCD, and/or LED technologies, an optical see-through display, an optical see-around display, a video see-through display, or other technologies now known or later developed. The processor 112 may receive data from the probe 104, and configure the data for display on the display screen of the user interface 110. User interface 110 may also be configured to generate audible output(s), via a speaker, speaker jack, audio output port, audio output device, earphones, and/or other similar devices.

Processor 112 may comprise one or more general purpose processors—e.g., microprocessors—and/or one or more special purpose processors—e.g., digital signal processors (DSPs), graphics processing units (GPUs), floating point units (FPUs), network processors, or application-specific integrated circuits (ASICs). In some instances, special purpose processors may be capable of image processing, image alignment, and merging images, among other possibilities. Data storage 114 may include one or more volatile and/or non-volatile storage components, such as magnetic, optical, flash, or organic storage, and may be integrated in whole or in part with processor 112. Data storage 114 may include removable and/or non-removable components.

Processor 112 may be capable of executing program instructions 124 (e.g., compiled or non-compiled program logic and/or machine code) stored in data storage 114 to carry out the various functions described herein. Therefore, data storage 114 may include a non-transitory computer-readable medium, having stored thereon program instructions that, upon execution by computing device 102, cause computing device 102 to carry out any of the methods, processes, or functions disclosed in this specification and/or the accompanying drawings. The execution of program instructions 124 by processor 112 may result in processor 112 using reference data 122. In one example, the reference data 122 may include a computer model that may be based on numerous designs of medical implants with known properties as well as bone structure and geometry holding the objects. In particular, the reference data 122 can include a database of finite element models of a plurality of medical implants that are commercially available. The reference data 122 can include a table of natural frequencies and/or linear stiffness coefficients for each of the plurality of medical implants, and the reference data 122 may further include a table of angular stiffness coefficients that correspond to the determined natural frequencies and/or linear stiffness coefficients. As such, and as discussed in additional detail below, the reference data 122 may be used to convert a measured response signal (e.g., the measured natural frequency and/or the linear stiffness coefficient of a medical implant) into an indication of stability of the medical implant. Particularly, the reference data 122 may provide a correlation between one or more natural resonance frequencies (or linear stiffness coefficients) and an angular stiffness coefficient value.

When in use, the drive signal source 116 may be configured to deliver an electrical driving signal to a distal end of the probe 104. The electrical driving signal may take various forms, such as impulse, sinusoid with a single frequency, sinusoid of increasing frequency (i.e., swept-sine), or random signals. This driving signal may be converted into a mechanical force by one or more transducers, such as piezoelectric transducers. Such a force may induce mechanical motion in the medical implant to which the force is applied. The mechanical motion may be detected via one or more transducers and a corresponding response signal may be sent back to the base station for processing and/or analysis. In another example, the probe 104 is configured to apply a vibration force to the medical implant, and the response signal corresponds to a motion of the medical implant in response to the applied vibration force.

In one embodiment, the response signal is provided to the spectrum analyzer 118, which may be configured to identify one or more characteristic frequencies in the signal. Such frequencies, known as natural frequencies, may be identified by converting the driving and response signals from a time domain representation in a frequency domain representation to obtain a frequency response function for example. A linear stiffness coefficient may also be identified using the same frequency response function. In another embodiment, an impedance analyzer is used to obtain impedance in the frequency domain. In yet another embodiment, the spectrum analyzer 118 is not needed. Instead, the driving and response signals are harmonic. Amplitude ratio of the response and driving signals is monitored to obtain a linear stiffness coefficient and natural frequencies.

The identified frequencies, or linear stiffness coefficients, or both may be further analyzed by the computing device 102 to calculate properties of the medical implant, as discussed in additional detail below. The computing device 102 may reside locally or in a network/cloud environment, and so does the computation. These properties can be used as a diagnostic standard to determine stability of the medical implant. In various embodiments, the result of any analysis, processing, or diagnosis may be displayed to a user via the display of the user interface 110.

In various embodiments, the computing device 102 may be configured to control various aspects of the system 100 such as the frequency of the signal applied via drive signal source 116 and probe 104, along with timing, input and output (I/O) of the spectrum analyzer 118 (e.g., input and/or output thereof), the input or output (I/O) associated with the display of the user interface 110 and the like. In addition, the computing device 102 may be configured to perform coefficient calculations and other data processing functionalities as discussed in additional detail below.

In some embodiments, the dental health detection system 100 may include many more components than those shown in FIG. 1. However, it is not necessary that all of these generally conventional components be shown in order to disclose an illustrative embodiment.

C. EXAMPLES OF METHODS

Figure 2:
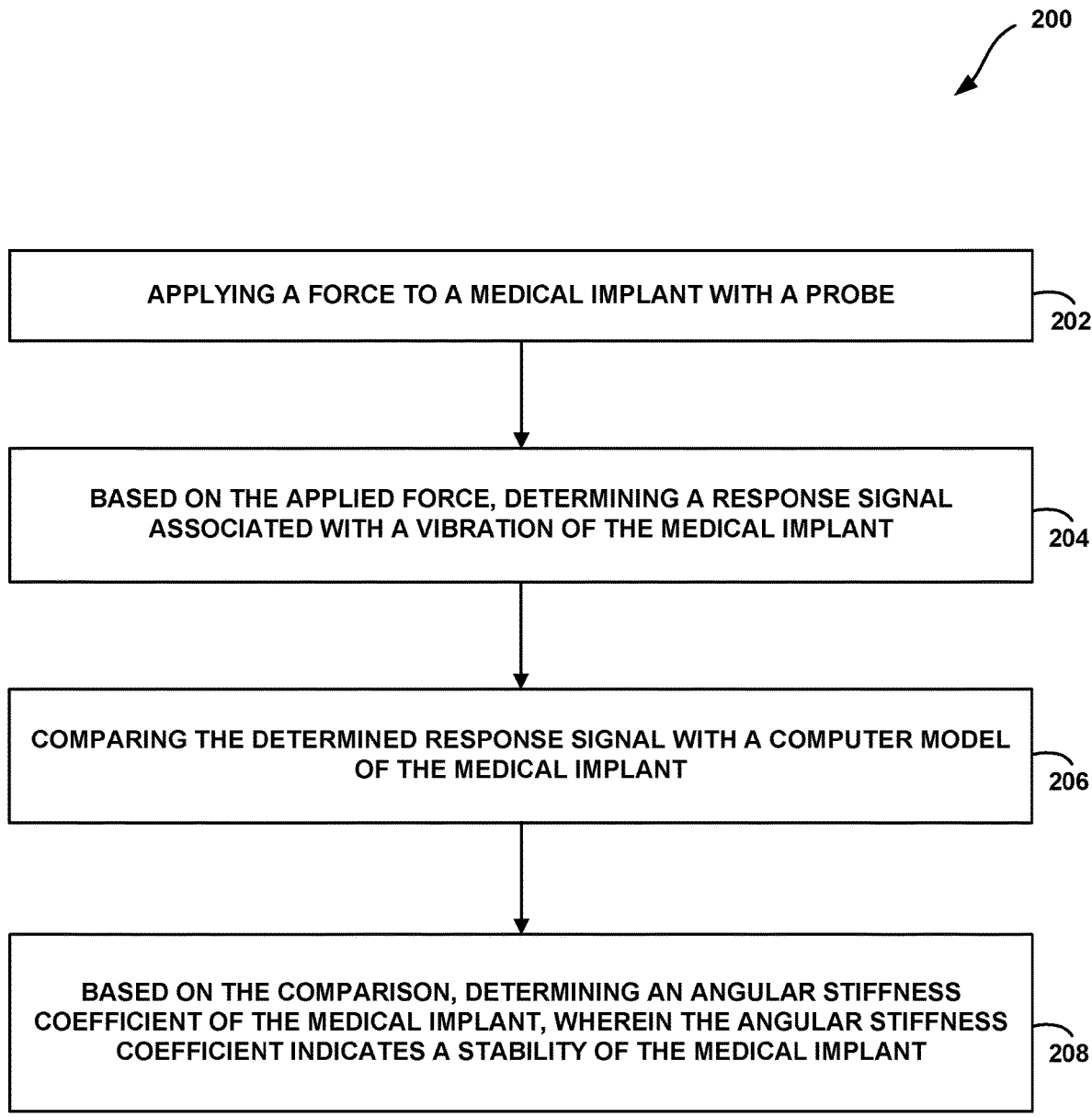
FIG. 2 a simplified flow chart illustrating a method, according to an example embodiment.

FIG. 2 is a simplified flow chart illustrating method 200 for detecting stability of a medical implant. Although the blocks in FIG. 2 are illustrated in a sequential order, these blocks may also be performed in parallel, and/or in a different order than those described herein. Also, the various blocks may be combined into fewer blocks, divided into additional blocks, and/or removed based upon the desired implementation.

Further, while the methods described herein are described by way of example as being carried out by a wearable computing device, it should be understood that an exemplary method or a portion thereof may be carried out by another entity or combination of entities, without departing from the scope of the invention.

In addition, the flowchart of FIG. 2 shows functionality and operation of one possible implementation of present embodiments. In this regard, each block may represent a module, a segment, or a portion of program code, which includes one or more instructions executable by a processor for implementing specific logical functions or steps in the process. The program code may be stored on any type of computer-readable medium, for example, such as a storage device including a disk or hard drive. The computer-readable medium may include non-transitory computer-readable medium, for example, such as computer-readable media that stores data for short periods of time like register memory, processor cache and Random Access Memory (RAM). The computer-readable medium may also include non-transitory media, such as secondary or persistent long term storage, like read only memory (ROM), optical or magnetic disks, compact-disc read only memory (CD-ROM), for example. The computer-readable media may also be any other volatile or non-volatile storage systems. The computer-readable medium may be considered a computer-readable storage medium, for example, or a tangible storage device.

For the sake of example, one or more steps of the method 200 shown in FIG. 2 will be described as implemented by a computing device, such as the computing device 102 in FIG. 1. It should be understood that other entities, such as one or more servers, can implement one or more steps of the example method 200.

At block 202, the method 200 includes applying a force to a medical implant with a probe. The medical implant may comprise one of a dental implant, a dental crown, a dental restoration, a bone screw, a plate, a hip implant, or a knee implant, as non-limiting examples. In one example, applying the force to the medical implant comprises generating a driving signal to excite the medical implant into vibration. In such an example, the response signal is based on the excited vibration of the medical implant in response to the driving signal. In another example, applying the force to the medical implant comprises applying a vibration force to the medical implant. In such an example, the response signal is based on motion of the medical implant in response to the vibration force. In another example, the method 200 further includes removably coupling an abutment to the medical implant. In such an example, the force is applied indirectly to the medical implant by applying the force to the abutment.

The amplitude of the applied force may be increased incrementally until critical physical properties, such as natural frequencies and linear stiffness coefficient, of the medical implant are detected with reasonable fidelity. The force may be applied, for example, by a piezoelectric transducer as further discussed below. The force may be applied in various and/or multiple directions relative to the medical implant, as multiple measurements may provide a better assessment of stability of the medical implant.

At block 204, the method 200 includes determining a response signal associated with a vibration of the medical implant based on the applied force. In one example, the response signal associated with the vibration of the medical implant comprises a natural frequency value. In another example, the response signal associated with the vibration of the medical implant comprises a linear stiffness coefficient. The response signal may be detected by one or more force sensors and/or vibrometers, as discussed in additional detail below. In particular, a motion in response to the applied force detected by one or more sensors and a corresponding response signal may be transmitted to a spectrum analyzer such as spectrum analyzer 118 discussed in connection with FIG. 1. The analyzer may process the received signals and provide frequency response information such as a frequency response curve showing how the medical implant responds over a range of frequencies for an applied force. A large number average of the received signals may be used in obtaining an accurate frequency response curve. The frequency response curve may show amplitudes of one or more frequency peaks associated with natural vibration modes of the medical implant. Also, the frequency response curve below the first natural frequency may be used to extract linear stiffness coefficients. In general, the frequency response curves may include an amplitude and a phase component for frequencies between 10 Hz and 6 KHz.

At block 206, the method 200 includes comparing the determined response signal with a computer model of the medical implant. In one example, the computer model is a finite element model of the medical implant. In general, natural frequencies and linear stiffness coefficients highly depend on various factors, such as the measurement locations and whether an abutment or a crown is present. Therefore, natural frequencies and linear stiffness coefficients, although measured, do not truly assess the stability of the medical implant. A more rigorous and robust quantity is angular stiffness of the entire medical implant-tissue-bone system. The angular stiffness, however, is difficult to measure directly. Therefore, a mathematical model is needed to extract the angular stiffness of the medical implant-tissue-bone system from the measured natural frequencies and linear stiffness.

Such a computer model may be based on numerous designs of medical implants with known properties as well as bone structure and geometry holding the objects. In particular, the computer model can include a database of finite element models of a plurality of medical implants that are commercially available. In particular, the computer model can include a table of natural frequencies and/or linear stiffness coefficients for each of the plurality of medical implants, and the database may further include a table of angular stiffness coefficients that correspond to the determined natural frequencies and/or linear stiffness coefficients. In such an example, comparing the determined response signal with the computer model of the medical implant comprises comparing the determined natural frequencies and/or linear stiffness coefficients with the table in the database of the computer model.

At block 208, the method 200 includes, based on the comparison of the determined response signal with the computer model, determining an angular stiffness coefficient of the medical implant, wherein the angular stiffness coefficient indicates a stability of the medical implant. As such, the method 200 uses the computer model to convert the measured response signal (e.g., the natural frequencies and/or the linear stiffness coefficient) into an indication of stability of the medical implant. Particularly, the computer model may provide a correlation between one or more natural resonance frequencies (or linear stiffness coefficients) and an angular stiffness coefficient value. As described above, the computer model can include a table of natural frequencies and/or linear stiffness coefficients for each of a plurality of medical implants, and the database may further include a table of angular stiffness coefficients that correspond to the determined natural frequencies and/or linear stiffness coefficients. In such an example, the angular stiffness coefficient may be determined for the medical implant in its surrounding bone or soft tissue by matching the measured natural frequency or linear stiffness information to those predicted by the finite element model.

As discussed in additional detail below, the angular stiffness coefficient may be determined by applying a pair of forces, equal in magnitude and opposite in directions, to form a couple (i.e., a moment) in the finite element model. The rotation of the center line may then be calculated. The ratio between the moment and the rotation is the angular stiffness coefficient.

The medical implant includes a longitudinal axis extending from a first surface of the medical implant to a second surface opposite the first surface along the center line of the medical implant. The longitudinal axis may be defined along and/or parallel to a longest dimension of the medical implant. In one embodiment, the second surface of the medical implant is implanted in a bone of a patient (e.g., a jaw bone if the medical implant is a dental implant), and the first surface of the medical implant is exposed and not physically coupled to the bone. The medical implant further includes a second axis that is perpendicular to the longitudinal axis. The angular stiffness coefficient may correspond to a stiffness of a rotation of the medical implant with respect to the second axis.

The angular stiffness coefficient as obtained above may be used to determine the stability associated with the medical implant in question. For example, a value of the coefficient may vary between stable and unstable medical implants. A high value of the angular stiffness coefficient may represent a stable medical implant, while a low angular stiffness coefficient value may represent an unstable or unsecure medical implant. A direct indication of the angular stiffness coefficient may be provided to a clinician by a display (such as the display of the user interface 100 of the computing device 102 in FIG. 1), or some other audible or visible indicator. In one example, the direct indication of the angular stiffness may provide a score between 1 and 100, with 1 being very unstable and 100 being very stable. In another example, the direct indication of the angular stiffness may provide a green, yellow, or red indicator on a display, where the green indicates a very stable medical implant, yellow indicates an average stability of the medical implant, and red indicates an unstable medical implant. An indirect indication of the coefficient may also be provided, such as binary good or bad indicator determined, for example, based on whether the coefficient exceeds a predetermined threshold. In yet another example, a given medical implant may be examined over time, and angular stiffness coefficients determined at different times may be compared with one another to thereby determine if the medical implant is becoming less stable over time. A large database of the angular stiffness coefficients may be collected and compared to facilitate big-data applications, such as wellness predictions during a healing process.

D. EXPERIMENTAL EXAMPLES

Example 1

Materials and Methods:
Simulated Jawbone:
Sawbones® (Vashon Island, WA) of three different densities were used. (1) Hybrid blocks (34×34×42 mm) mimicking average human mandible density (Ahn, et al. 2012, Tabassum, et al. 2010) consisted of a 40-mm thick block (20 PCF, 0.32 g/cc) resembling trabecular bone and a 2-mm laminate (40 PCF, 0.64 g/cc) representing cortical bone. (2) High-density blocks (34×34×40 mm, 40 PCF, 0.64 g/cc) representing Type I bone according to Lekholm and Zarb bone classification system (Jeong, et al. 2013, Lekholm, et al. 1985). (3) Low-density blocks (34×34×40 mm, 15 PCF, 0.24 g/cc) representing Type III-IV bone.
Dental Implants:
Branemark® Mk III implants (Groovy, Nobel Biocare, Switzerland) in two different implant widths were used: (a) regular platform (RP), 4 mm in width by 8.5, 10, 11.5, 13, 15 and 18 mm length, and (b) wide platform (WP), 5 mm in width by 8.5, 11.5, 15 and 18 mm length. Branemark® RP implants of various lengths were positioned in the center of the three-different density Sawbones® blocks. Implants were placed following the manufacturer's surgical protocol and inserted to 45 N·cm. Because WP implants are often used more in low-density bone, the WP Branemark® implants of different lengths were placed in 15 PCF Sawbones® blocks and torqued to 45 N·cm. Healing abutments (HA) 7 mm in length were used for the RP implants, while HA 5 mm in length were used for the WP implants. A 10 N·cm torque was used to secure the HA with the Branemark System Torque Control (Nobel Biocare, Sweden).
Boundary Conditions:
All samples were secured at the bottom of the block. The bottom surfaces of the Sawbones® samples were attached to a steel block (63.5×63.5×14.5 mm in dimension) using carpet tape. The steel block was clamped firmly in a vise. The goal was to create a fixed boundary condition at the bottom surface of the Sawbones® specimen.
Measurement Methods:
The implants were tested using experimental modal analysis (EMA). Essentially, the setup consisted of a force hammer, a laser Doppler vibrometer (LDV) and a spectrum analyzer. The hammer measured the force applied to the implant, and the LDV measured the velocity response of the implant. Based on the measured force and velocity, the spectrum analyzer calculated frequency response functions (FRF) from which natural frequencies of the implant-Sawbones® test models were extracted. The average linear stiffness of implantabutment-Sawbones® for each sample was extracted from the FRF as follows.
(a) Linear Stiffness Coefficients:
Stiffness is the rigidity of an object. It describes the relationship between an applied load on a structure and the responding displacement. Stiffness depends on the location and type of the load as well as the displacement. Two common forms of stiffness are linear stiffness and angular stiffness.

For linear stiffness, the load is a force F and the structural response is a linear displacement x. The applied force is proportional to the displacement, and the ratio is the linear stiffness coefficient k, i.e., $$k = F/x \qquad (1)$$

Figure 3:
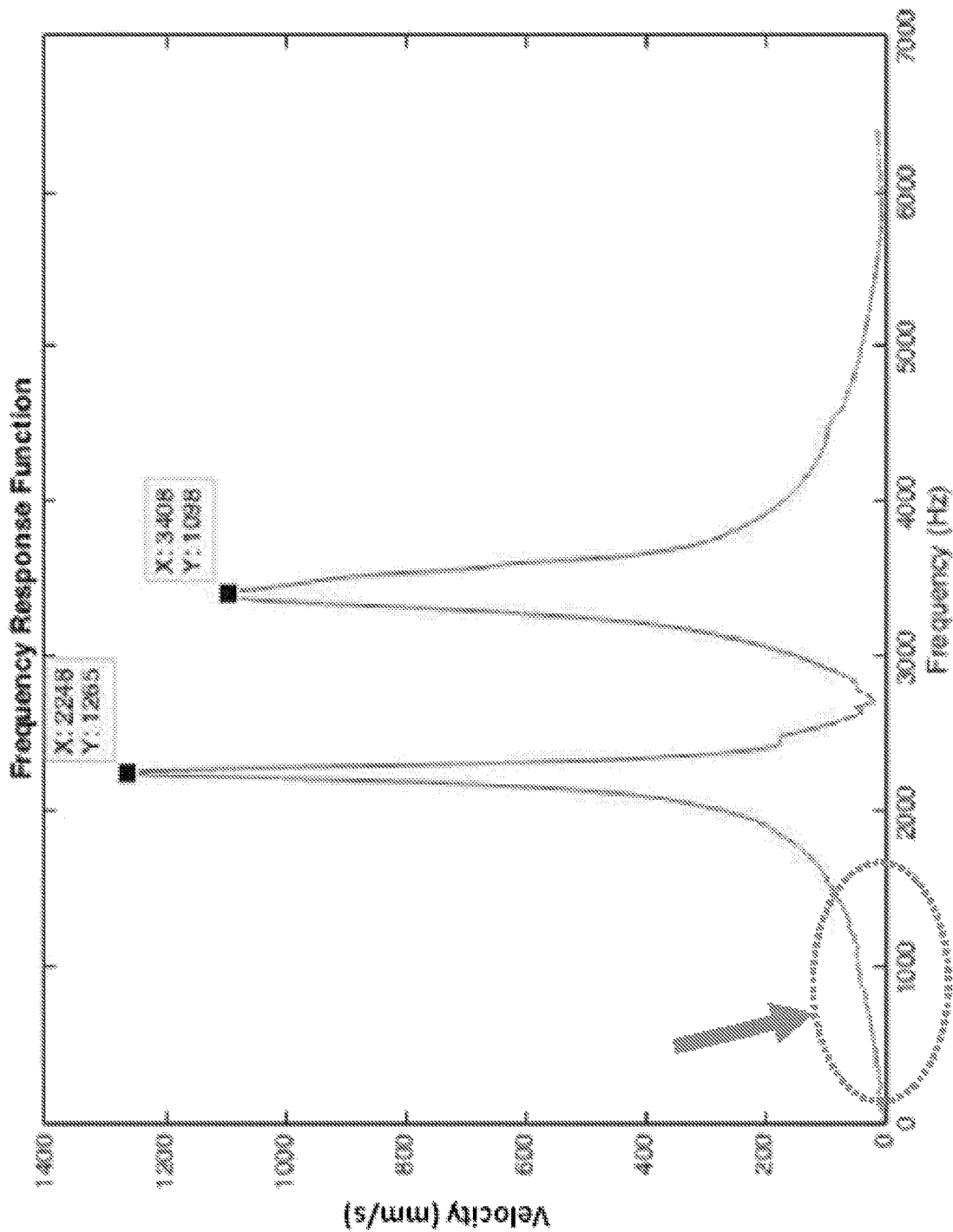
FIG. 3 is a graph of an example linear stiffness estimation, according to an example embodiment.

The linear stiffness coefficient k can be estimated in the frequency domain. Theoretically, the FRF (with force input and velocity output) should increase linearly when the frequency is significantly less than the first natural frequency. This corresponds essentially to the area of the graph (flat region) before the first peak (i.e., in the frequency range before it hits the first peak) as shown in FIG. 3. Moreover, the slope of the FRF is the reciprocal of the linear stiffness coefficient k of the measured implant-bone-abutment assembly. This is however a somewhat less robust measurement (compared with natural frequencies) because the measured frequency response function may not truly have a linearly increasing region due to measurement errors. Meaning the area before the first peak may not always be linear, which makes it difficult to estimate the linear stiffness. Also, the linear stiffness coefficient k estimated depends on the location where the hammer strikes and the laser is directed, which may vary between specimens. Nevertheless, it is a measurable quantity that should be interpreted carefully.

Angular Stiffness Coefficients:

For angular stiffness, the load is an applied moment M and the structural response is an angular displacement $\theta$. The applied moment is proportional to the angular displacement, and the ratio is the angular stiffness coefficient $k_\theta$, i.e., $$k\theta = M/\theta \quad (2)$$

Figure 4:
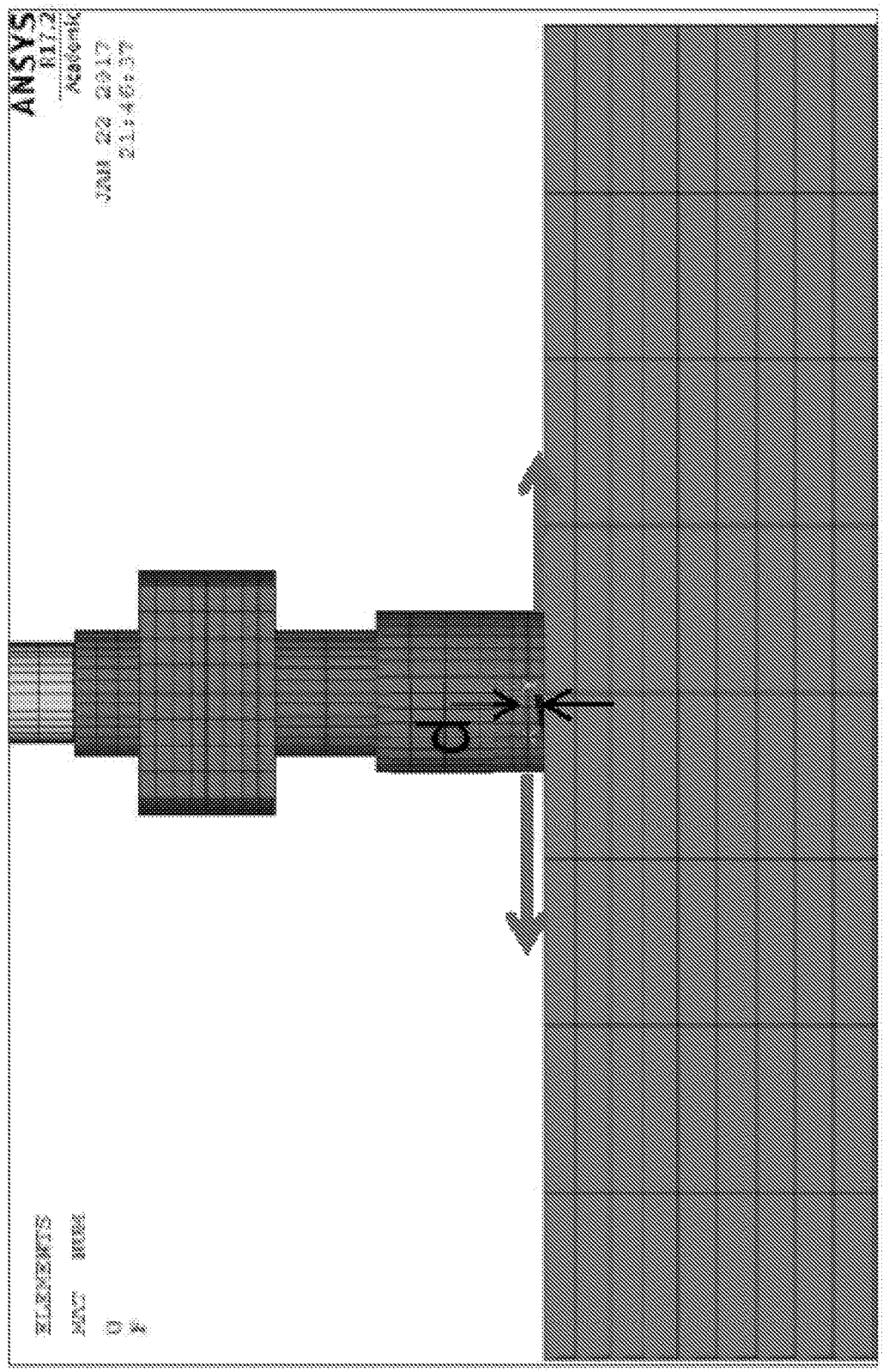
FIG. 4 is an example applied moment to predict angular stiffness in a finite element model of a medical implant, according to an example embodiment.

The angular stiffness coefficient is an ideal representation of dental implant stability. In theory, when a moment is applied at the base of an abutment, the moment does not deform the abutment elastically. The response is entirely from the bone-implant interfacial stiffness and the elasticity of the implant. The angular stiffness is an excellent way to quantify dental implant stability, because it completely removes the effects of the abutment. Such an arrangement is shown in FIG. 4.

The angular stiffness coefficient $k_\theta$, however, is quite difficult to measure experimentally. Application of torque to the implant without incurring any abutment deformation is unattainable. Also, angular displacement is difficult to measure accurately. Thus, as described herein a combined approach is used to estimate the angular stiffness coefficient $k_\theta$. Initially, natural frequencies are measured directly via experiments. Then, an accurate mathematical model (e.g., via FEA) may be used to convert the measured natural frequencies to estimate the angular stiffness coefficient $k_\theta$.

Finite Element Analysis:

A three-dimensional (3-D) finite element model was created using ANSYS R-15 (Canonsburg, PA) to simulate the Branemark® implants, the experimental setup, and the test results. Material properties of each component such as Sawbones® and implants published by manufacturers were used in the finite element model. The model includes two types of abutments: healing abutment (HA) 7 mm in length and impression coping abutment (IMP) 12 mm in length. The HA was used to verify the experimental measurements, whereas the IMP was used to demonstrate the validity of quantifying implant stability via the angular stiffness coefficient $k_\theta$.

After the model was created, a modal analysis was first conducted to calculate the natural frequencies. Then a static analysis was performed to calculate linear and angular stiffness coefficients k and $k_\theta$. To calculate the linear stiffness coefficient k, a force was applied to a node where in the experiment the impact hammer contacted. The displacement of a node where the LDV measured experimentally was then predicted via FEA. The ratio of the force and the displacement predicted the linear stiffness coefficient k. To calculate the angular stiffness coefficient $k_\theta$, a pair of equal and opposite forces was applied to two neighboring nodes at the base of the abutment to form a couple, as shown in FIG. 4. The rotation of the centerline of the abutment at its base was the angular displacement. The ratio between the couple and the angular displacement gave the angular stiffness coefficient $k_\theta$.

Figure 5:
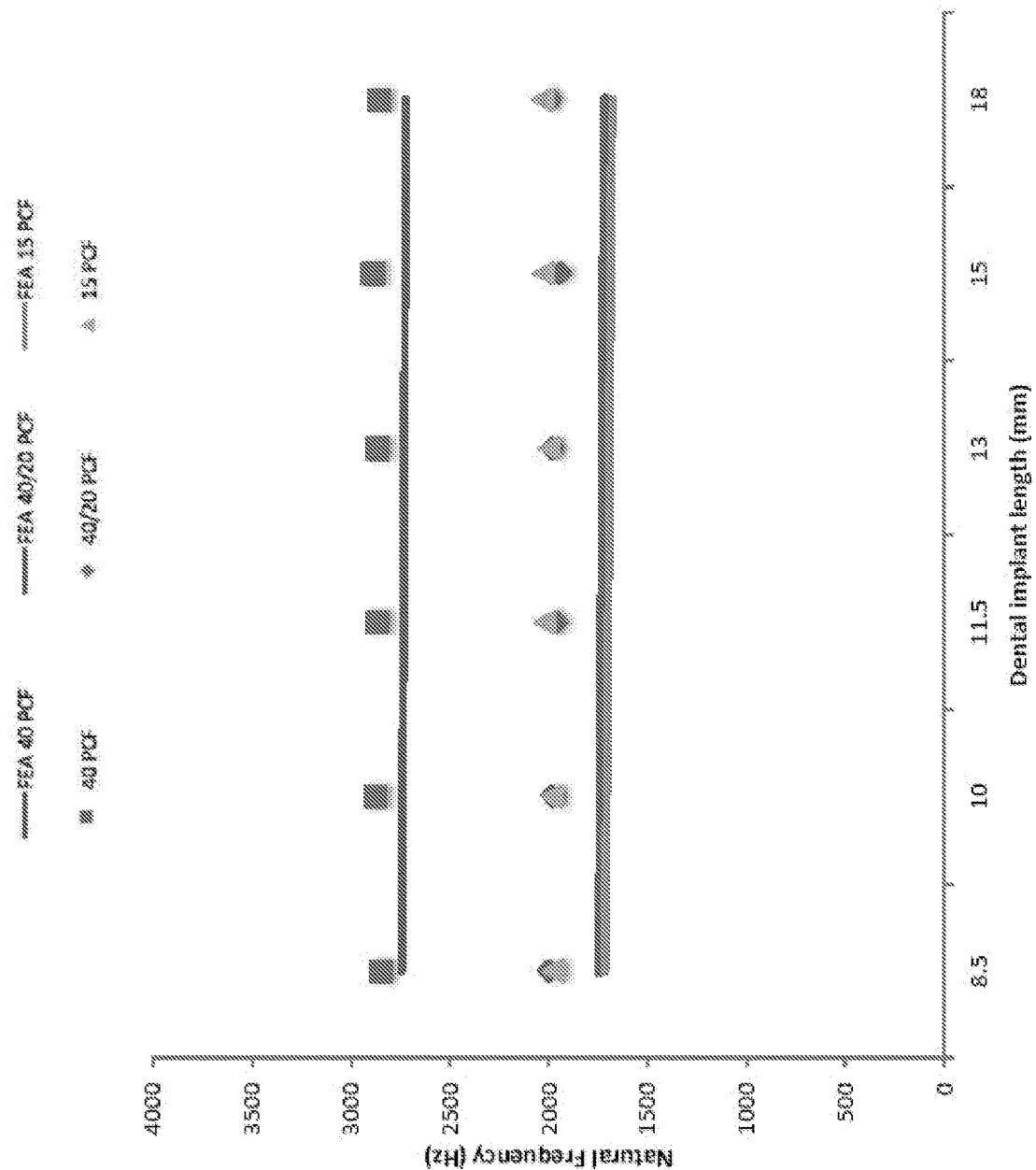
FIG. 5 is a graph of natural frequencies of a medical implant vs. implant length, according to an example embodiment.

Results:

1. Experimental Modal Analysis Results for Regular Platform Implants:

For Branemark® RP implants with HA, FIG. 5 shows the measured first natural frequencies versus the implant length. The measured natural frequencies ranged between 2848 and 2888 Hz for the high-density blocks, 2112 and 2176 Hz for the hybrid blocks, and 1936 and 2036 Hz for the low-density blocks. The measured natural frequencies did not have a significant correlation to the implant length.

Figure 6:
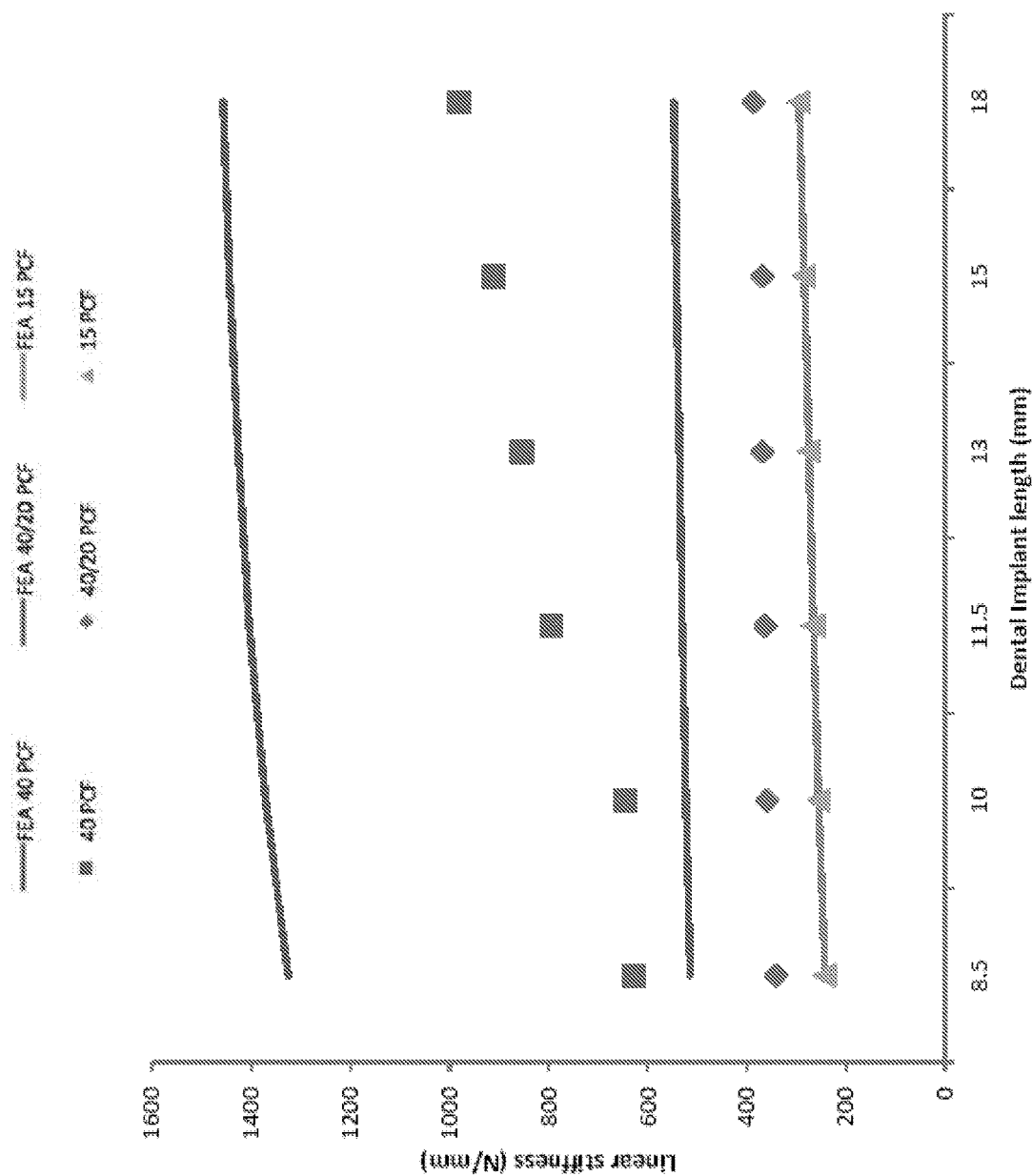
FIG. 6 is a graph of linear stiffness of a medical implant vs. implant length, according to an example embodiment.

FIG. 6 shows the linear stiffness coefficients extracted from the measured frequency response functions. The linear stiffness coefficient for the high-density blocks ranged from 628.6 to 980.1 N/mm for the high-density blocks, from 329.5 to 386.7 N/mm for the hybrid blocks, and from 169.8 to 271.5 N/mm for the low-density blocks, see FIG. 6.

In general, the stiffness had a similar trend to the natural frequencies where the high-density blocks are significantly higher in stiffness and natural frequencies than those of the hybrid and low-density blocks. The low-density and hybrid blocks had closer linear stiffness coefficients and natural frequencies. The linear stiffness coefficient of the high-density blocks increased with increasing implant length, while the linear stiffness coefficient of the low and hybrid density blocks did not vary significantly with implant length.

Figure 7:
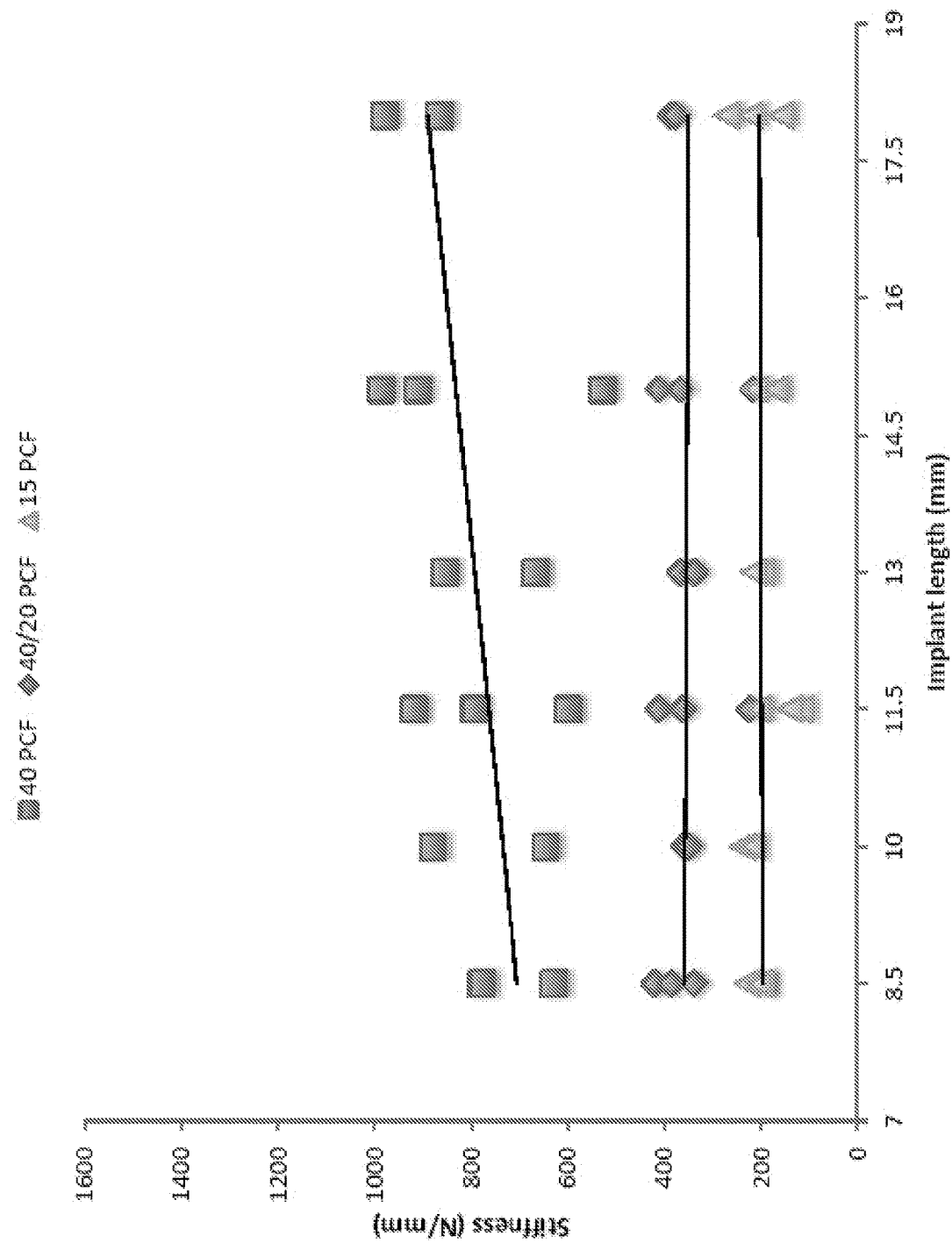
FIG. 7 is a graph of repeatability results showing variations of extracted linear stiffness coefficients, according to an example embodiment.

To evaluate the repeatability and consistency of the estimated linear stiffness coefficients the experiments were repeated. FRF results from multiple EMA were used to estimate the average linear stiffness. The linear stiffness coefficient was estimated from FRFs of the Branemark® RP implants that had consistent natural frequency measurements. The results are demonstrated in FIG. 7. The linear stiffness coefficients varied widely especially for the high-density blocks but were within the same range for the hybrid and low-density blocks. Two important points need to be emphasized. First, this shows how linear stiffness can be a hard parameter to estimate as it depends on the location of where the hammer taps and the laser is aimed, which can vary from one test to another no matter how much the parameters are attempted to be constant. Second, detecting the low-stiffness cases is critical clinically as these are the conditions of a failing implant.

2. Finite Element Analysis for Regular Platform Implants:

(a) Natural Frequencies:

Natural frequencies predicted by FEA are presented in FIG. 5 for comparison. The three solid lines represent the FEA predictions of natural frequencies for hybrid, high-density, and low-density blocks. In general, the predicted natural frequencies agree well with the measured natural frequencies within 10%. The high-density blocks showed better agreement than the low-density and hybrid blocks. Moreover, the FEA predictions and the EMA measurements had the same trend. For example, natural frequencies showed no correlation to the implant length. Also, natural frequencies of the hybrid blocks and low-density blocks were about the same.

Therefore, the close agreement between the FEA predictions and EMA measurements in natural frequencies indicates that the finite element model is very accurate. Note that the FEA predictions and EMA measurements were not the same due to variable in the experiments such as variations of material properties of Sawbones® and contact conditions at the implant-Sawbones® interface, as shown in FIG. 5.

Figure 8:
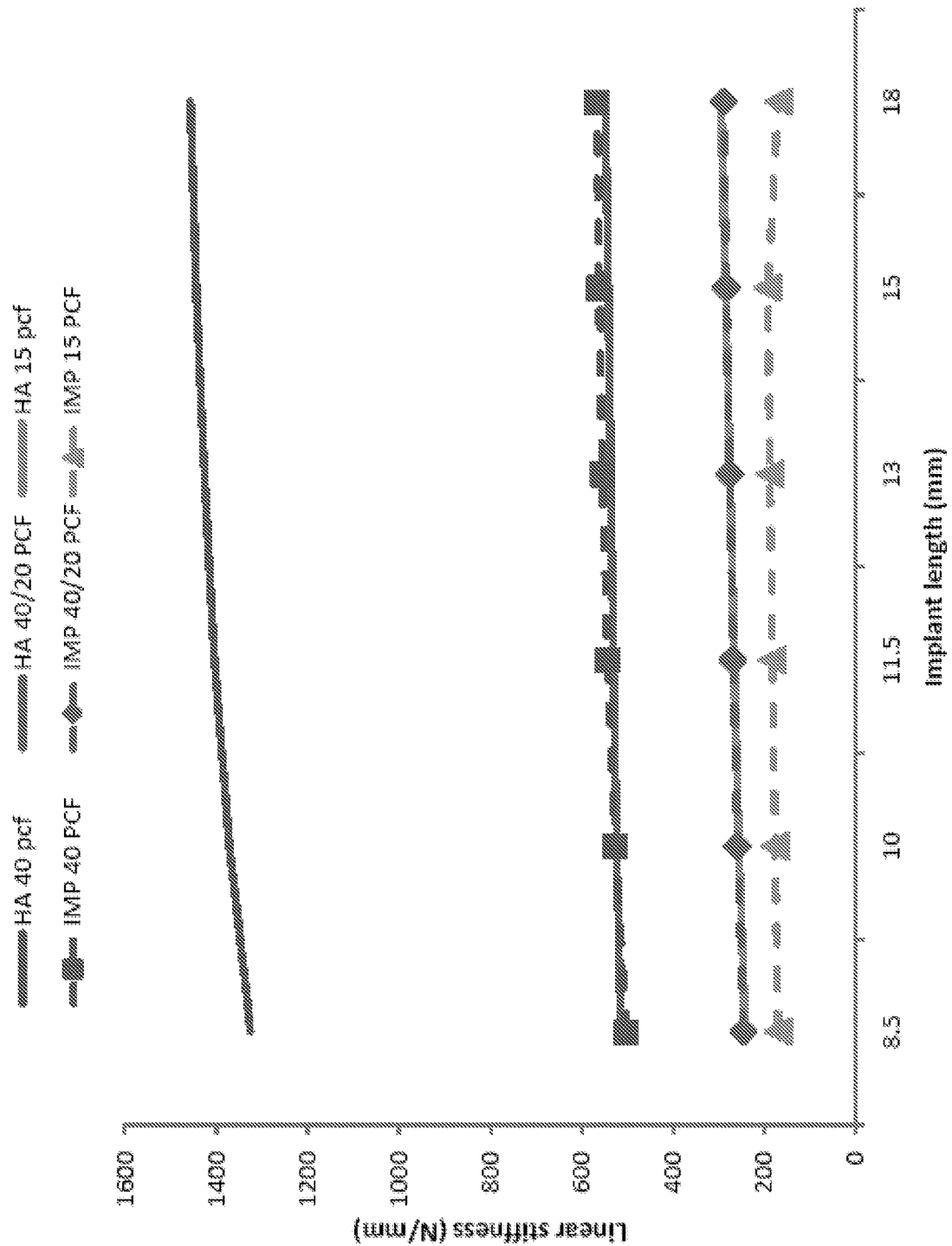
FIG. 8 is a graph showing finite element analysis prediction of stiffness compared to linear stiffness coefficients, according to an example embodiment.

(b) Linear Stiffness:

Linear stiffness coefficients predicted by FEA are shown in FIG. 8 for comparison as well. There are several things to note. First, the FEA predictions have the same trend as the EMA results. Specifically, the linear stiffness coefficient of the high-density block tends to increase with increasing implant length. In contrast, the linear stiffness coefficients of the low-density and hybrid blocks are closer to each other, and do not vary significantly with respect to the implant length, as shown in FIG. 6. The FEA predictions capture all these features observed in the EMA measurements. Second, the predicted linear stiffness coefficients are higher than the measured ones. For the low-density Sawbones®, the predicted and measured linear stiffness coefficients are close. For the high-density Sawbones®, the difference between the predicted and measured linear stiffness coefficients, albeit large, is with the same order of magnitude.

As explained above, it is known that linear stiffness is a less robust quantity than natural frequencies measured by EMA. It is very susceptible to test conditions (e.g., location of the hammer taps), and it has a much smaller signal-to-noise ratio compared with natural frequency measurements. Therefore, it is not realistic to expect that numerical values of the linear stiffness from the FEA predictions and EMA measurements agree well. Nevertheless, the comparison in FIG. 6 shows two encouraging signs. First, the FEA results predict the trend. That, again, indicates that the finite element model is accurate. Second, the biggest difference between the predicted and measured linear stiffness coefficients is around 100% (e.g., 1300 vs. 620 N/nm for 8.5 mm implant in high-density block). The difference is not too bad insofar as using an impact hammer to measure stiffness.

The finite element model also proves that linear stiffness coefficients are not good indicators to define implant stability, because they heavily depend on abutment geometry. FIG. 8 compares the FEA predictions of the linear stiffness coefficients with an HA and with an IMP abutment. The change from HA to the IMP abutment does not change the trend of the linear stiffness coefficients with respect to the implant length. The linear stiffness coefficients with the IMP abutment, however, are significantly lower, as shown in FIG. 8. This indicates that the elasticity of the IMP abutment has affected the linear stiffness. Therefore, linear stiffness is not a representative measure of the implant-bone interface stiffness or the stability of the implant.

Figure 9:
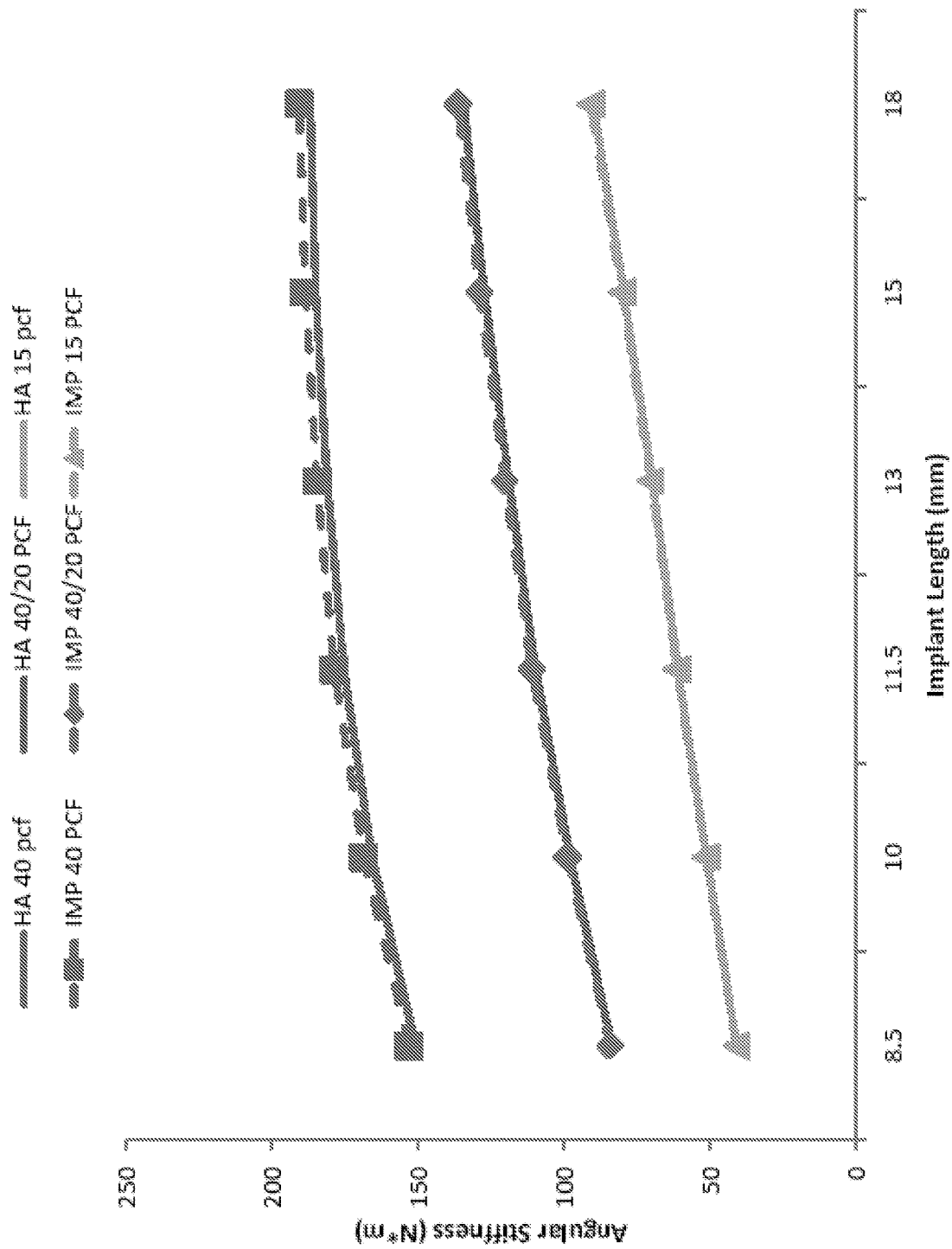
FIG. 9 is a graph showing finite element analysis prediction of stiffness compared to angular stiffness coefficients, according to an example embodiment.

(c) Angular Stiffness:

The FEA model allows us to calculate angular stiffness coefficients. FIG. 9 compares angular stiffness coefficients predicted by the FEA with HA and IMP abutments. When a moment is applied at the cervical area of the dental implant or the base of the abutments (HA and IMP) with Branemark® RP in hybrid blocks, we notice that the angular stiffness coefficients are quite similar with minimal difference for implants with both abutments, less than 1.5%. This shows how the angular stiffness coefficient at the base or apical region of the abutment is independent of the length of the abutment and can represent the dental implant stability more accurately. The angular stiffness coefficients tend to increase significantly with increasing implant length, as shown in FIG. 9.

3. Stability of Wide Platform Implants:

The EMA and FEA procedure developed above can be applied to WP implants to determine their_stability. Moreover, the stability can be compared with that of the RP implants for an evaluation. Note_that the WP implants are measured only in low-density blocks. Therefore, the comparison is made with RP implants also in low-density blocks.

(a) Experimental Modal Analysis.

Figure 10:
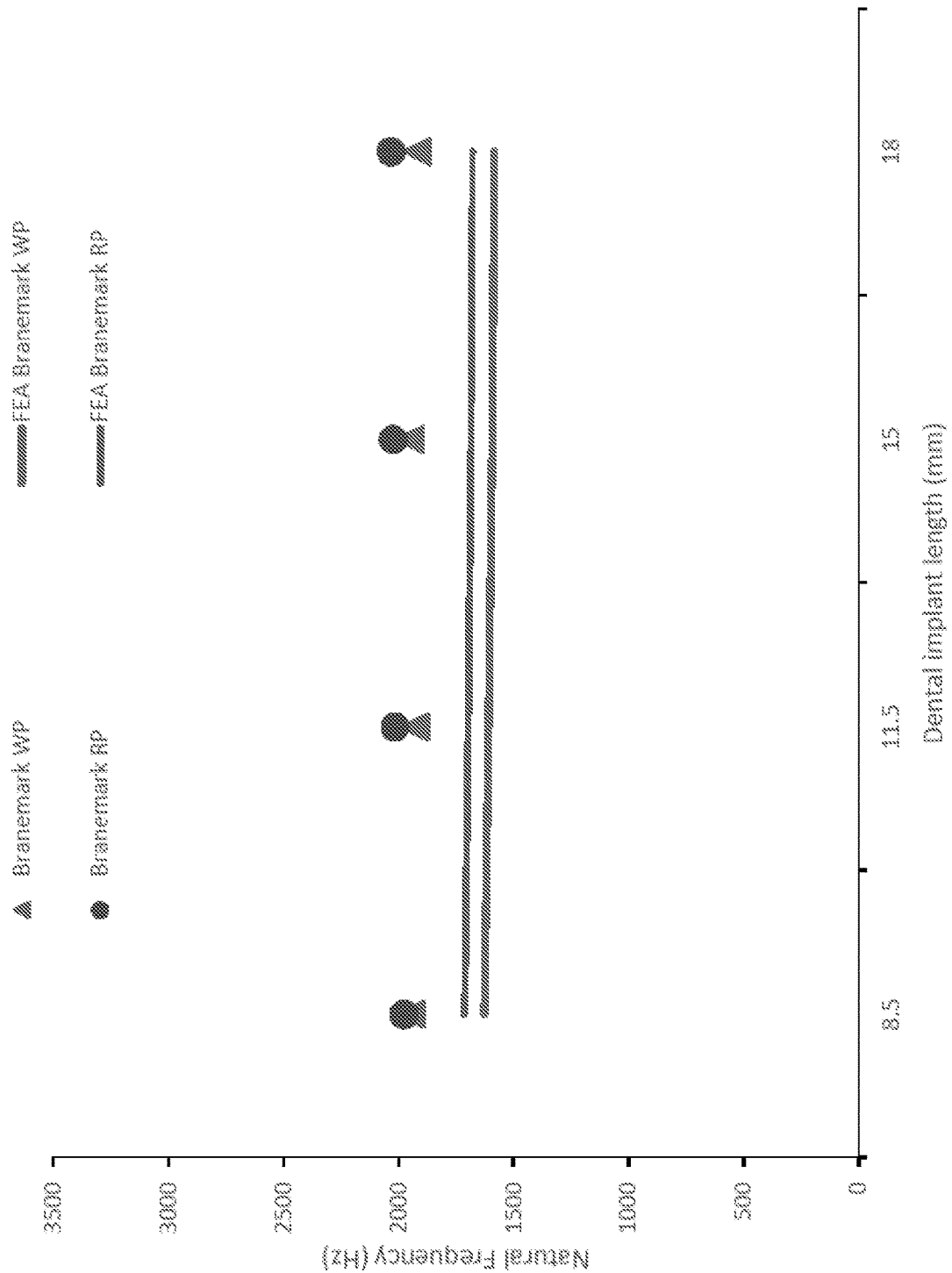
FIG. 10 is a graph showing finite element analysis prediction of stiffness compared to natural frequencies, according to an example embodiment.
Figure 11:
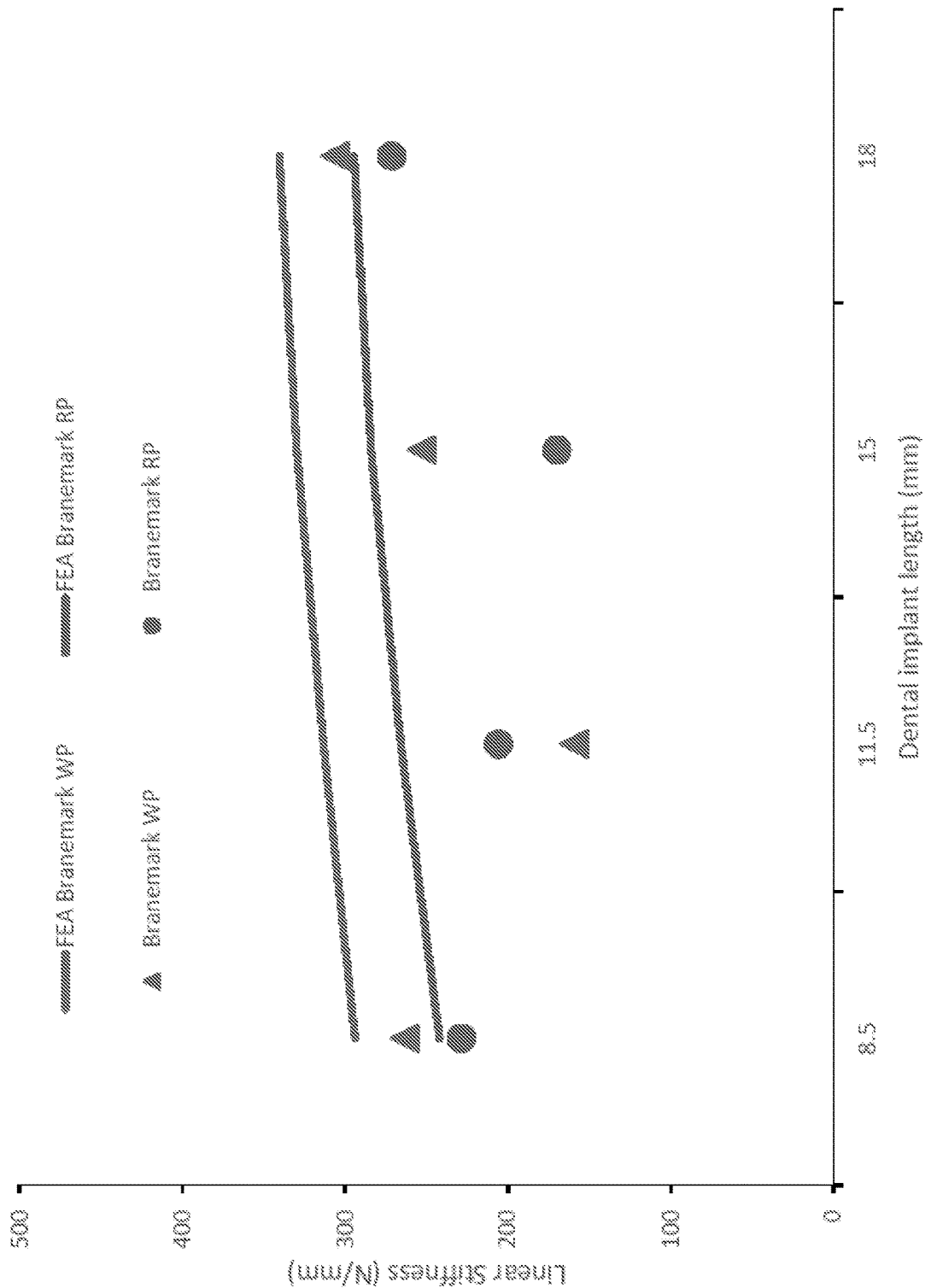
FIG. 11 is graph showing finite element analysis prediction of stiffness compared to linear stiffness coefficients, according to an example embodiment.

The first natural frequencies measured via EMA ranged from 1984 to 2072 Hz, as shown in FIG. 10. The natural frequencies were in the same range as those for the RP implants in low-density blocks. Therefore, varying the width does not cause a significant change in natural frequencies. In contrast, the linear stiffness coefficients varied from 346.7 to 429.6 N/mm, which are significantly higher than those extracted from the RP implants in low-density blocks, as shown in FIG. 11. It is now evident that natural frequencies are not representative of implant stability.

(b) Finite Element Analysis.

FEA is conducted on Branemark® WP implants with HA in low-density blocks. Natural frequencies predicted by the FEA are presented in FIG. 10 for comparison. The predicted natural frequencies agree well with the measured ones. The linear stiffness coefficients predicted by FEA for WP and RP implants are shown in FIG. 11 for comparison. Note that the predicted stiffness agrees well with the measured stiffness not only in magnitude but also in trend. For example, the predicted stiffness for WP is higher than that of RP.

Figure 12:
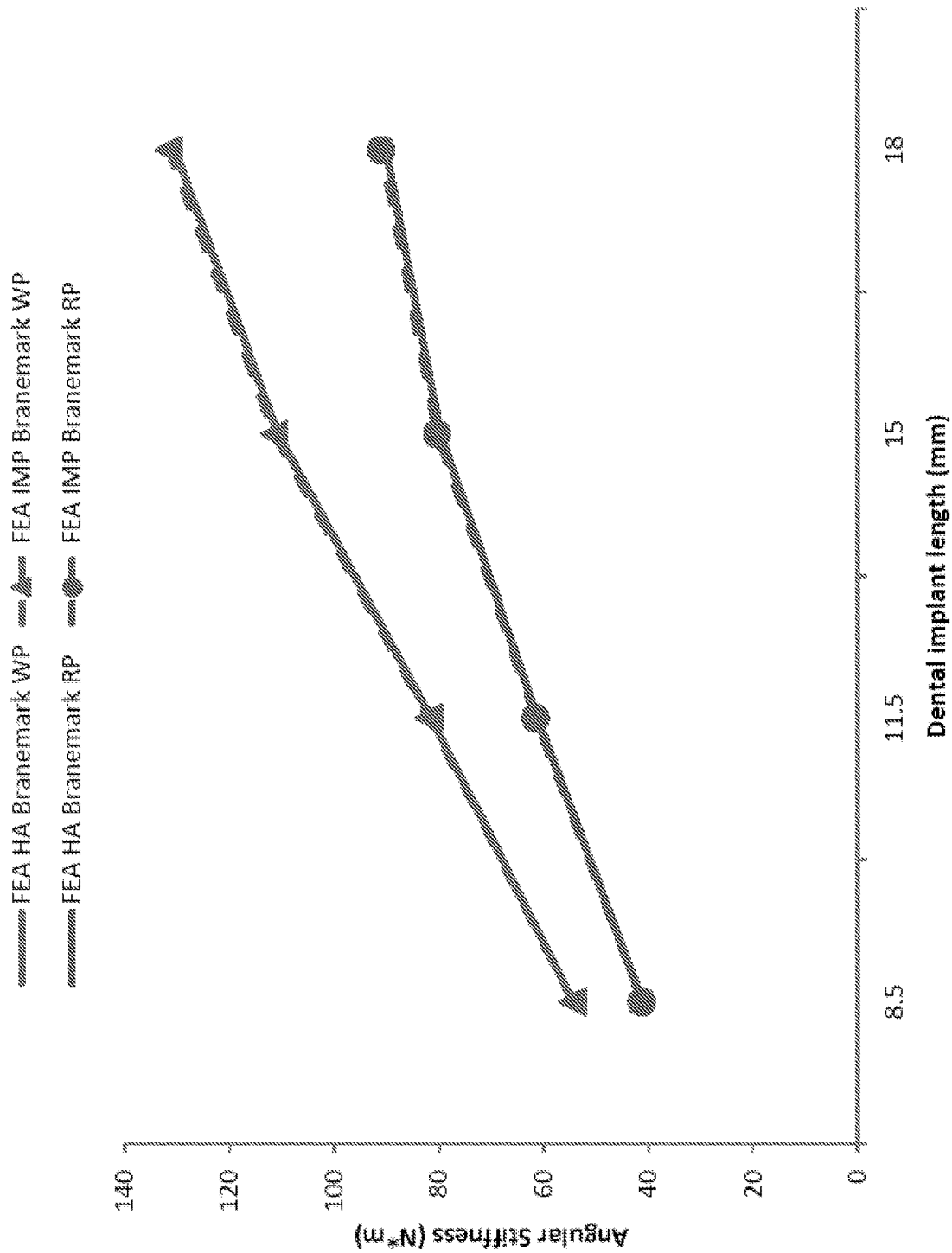
FIG. 12 is a graph showing finite element analysis prediction of stiffness compared to angular stiffness coefficients, according to an example embodiment.

The angular stiffness coefficient was predicted for Branemark® WP and RP implants in low-density blocks, as shown in FIG. 12. Also, both angular stiffness coefficients obtained from models with HA and IMP abutments are presented in FIG. 12. There are several observations. First, the angular stiffness coefficients from the HA and IMP abutments are almost identical, proving again that the angular stiffness coefficient is a robust quantity to represent implant stability. Second, WP implants tend to have significantly larger angular stiffness coefficients than the RP implants. Finally, the angular stiffness coefficients increase with increasing implant length for both WP and RP implants.

Example 2

Materials and Methods:
Simulated Jawbone:

Sawbones® (Vashon Island, WA) are synthetic polyurethane test blocks that come in different densities and forms to resemble the physical properties of human bone with ±10% precision. Three different Sawbones® densities were used: hybrid blocks, high-density blocks, and low-density blocks. Hybrid blocks (34×34×42 mm in dimensions) were used to mimic the average human mandible density. They consisted of a 40-mm thick block (20 PCF, 0.32 g/cc) resembling trabecular bone and a 2-mm laminate (40 PCF, 0.64 g/cc) resembling cortical bone. High-density blocks (34×34×40 mm, 40 PCF, 0.64 g/cc) were used to resemble type I bone according to the Lekholm and Zarb bone classification system. Low-density blocks (34×34×40 mm, 15 PCF, 0.24 g/cc) were used to resemble type III-IV bone.

Figure 13:
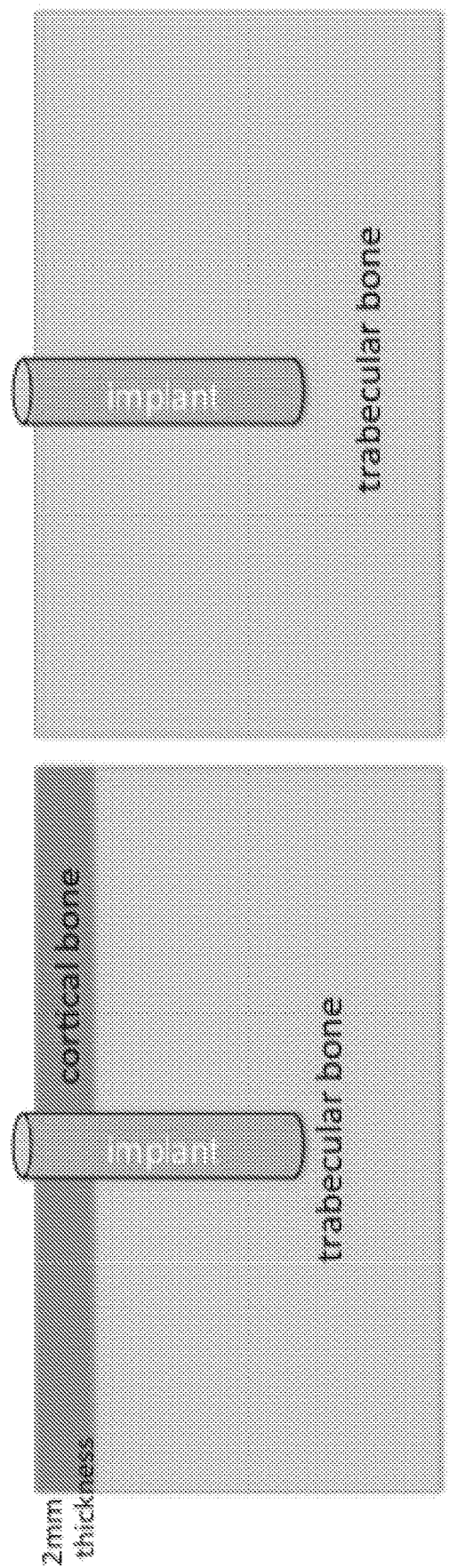
FIG. 13 is illustrates a simplified model of a dental implant, according to an example embodiment.

Dental Implants:

Branemark Mk III implants (Groovy, Nobel Biocare) in lengths of 7, 8.5, 10, 11.5, 13, 15, and 18 mm were place in the center of each block following manufacturer's surgical protocol seating to 45 N*cm as shown in FIG. 13. The lower 13-mm part of each block was fixed to a vise providing as much a fixed boundary condition as possible. The vise was attached on an isolation table via screws to reject as much vibration from ambient environments as possible. The implant-Sawbones systems were tested using Osstell ISQ®, Periotest®, and EMA. For the Osstell ISQ® tests, Smart Pegs (type I) were screwed on the implant at the fixture level with finger pressure. Measurements were taken mesio-distally (MD) and the mean was calculated. A 10 N*cm torque was used to tighten abutments with Branemark system Torque control. For the Periotest® measurements, the samples were tested with the device tip placed perpendicular to the access of the implant and a few millimeters away. The average of three readings was taken for each set of measurements and the abutment was removed and re-attached between measurements.

Figure 14:
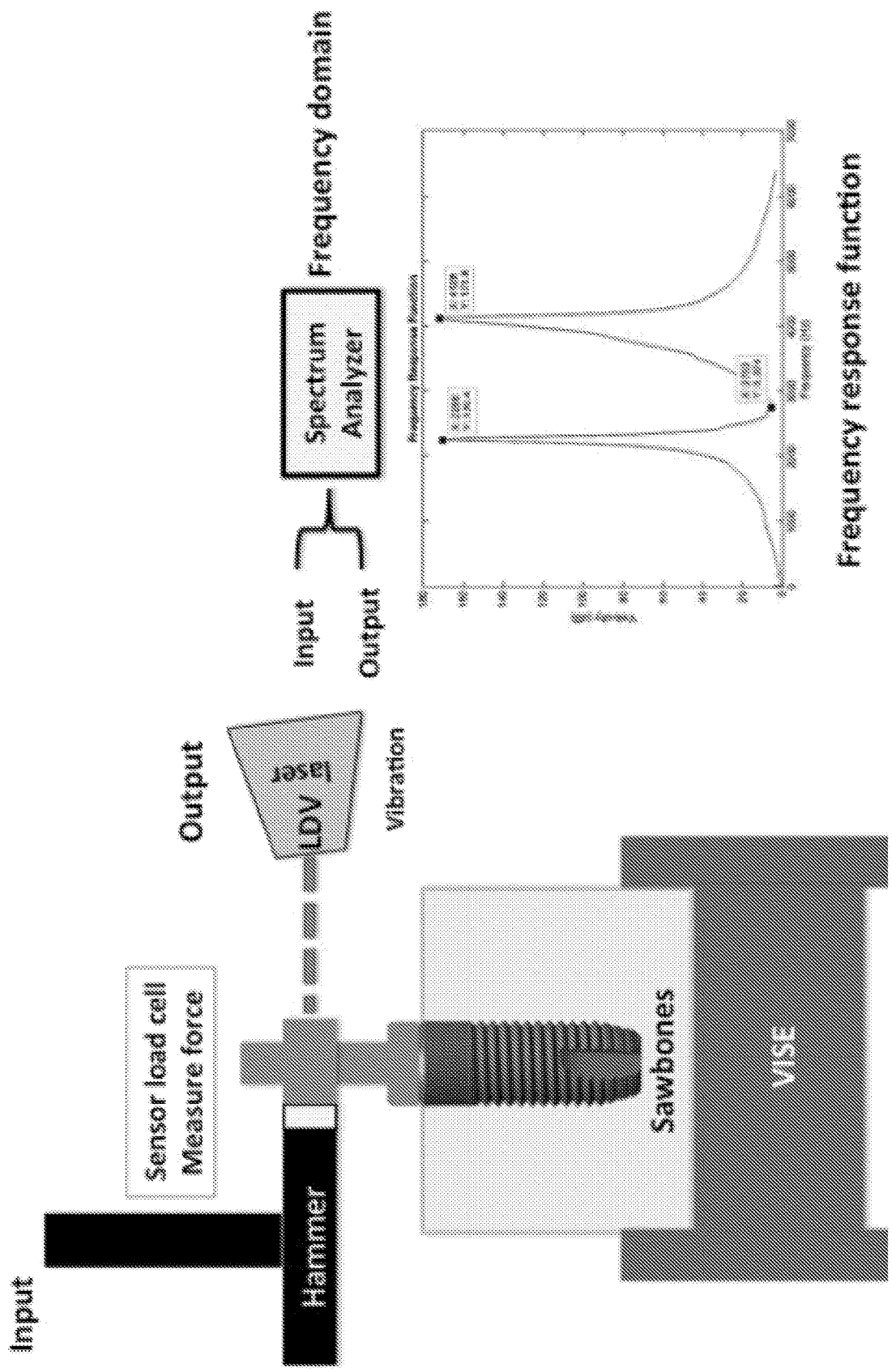
FIG. 14 is an experimental setup for modal analysis for testing dental implants, according to an example embodiment.

Experimental Setup for Experimental Modal Analysis:

The setup consisted of a hammer (PCB Piezotronics Inc., Depew, NY), a laser Doppler vibrometer (LDV) (Polytec Inc., Dexter, MI), and a spectrum analyzer (Stanford Research Systems, model SR785, Sunnyvale, CA), as shown in FIG. 14. The hammer tapped the abutment causing the dental implant to vibrate. At the tip of the hammer, a load cell (force sensor) measured the force acting on the abutment. In the meantime, LDV measured the vibration velocity of the dental implant and its abutment. The measured force and velocity data were fed into the spectrum analyzer, where a frequency response function was calculated in the frequency domain. Various parameters (e.g., natural frequencies, viscous damping factors, and stiffness) can be extracted from the measured frequency response function.

Extraction of Natural Frequencies:

The frequency corresponding to a peak in the measured frequency response functions is a natural frequency. In general, natural frequencies are very robust quantities in EMA. They are easy to measure and the measurements are quite repeatable. Since natural frequencies depend on stiffness, their value depends on various factors that affect the stiffness, such as material and geometry of the implants and Sawbones®, orientation of the implant with respect to the Sawbones®, interfacial properties between the implant and the Sawbones®, boundary conditions of the experimental setup (e.g., fixture and how Sawbones® blocks are held), and others (e.g., residual stresses).

Figure 15B:
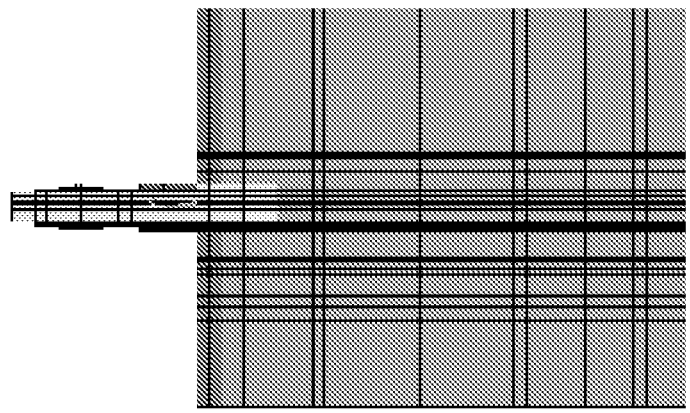
FIG. 15B is a two-dimensional side cross-section view of the dental implant of FIG. 15A, according to an example embodiment.
Figure 15A:
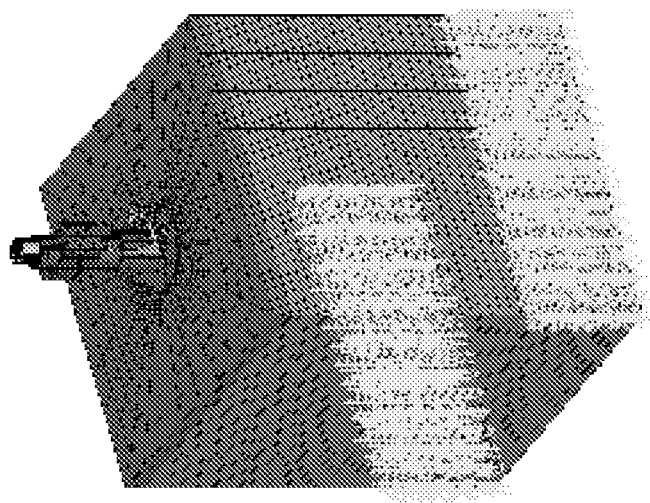
FIG. 15A is a three-dimensional finite element model of a dental implant embedded in a block, according to an example embodiment.

Finite Element Analysis:

A three-dimensional (3-D) finite element model was created using ANSYS R-15 (Canonsburg, PA) to simulate the experimental setup and the test results, as shown in FIGS. 15A-15B. The model was built using SOLID186 elements, which are higher-order, 3-D, 20-node solid elements that assume quadratic displacement fields. The finite element model consists of three parts: a Sawbones® block, a cylindrical implant, and an impression coping abutment. For the Sawbones® block, material properties (e.g., density and Young's modulus) provided by the manufacturer were used to model the tested Sawbones® blocks of three different densities. The Sawbones® block was assumed to be isotropic and has the same size as the test samples. Moreover, the block was fixed at two sides for the lower 13 mm to reflect the boundary conditions imposed in the experiments. To model the implant, one-piece cylinders 7, 8.5, 10, 11.5, 13, 15, and 18 mm in length and 4 mm in diameter were used. Material of the cylinders was titanium alloy $Ti_4Al_6V$. Moreover, the cylinders were located at the center of each Sawbones® block. The nodes of the cylindrical implants and the Sawbones® block are merged at the implant-Sawbones® interface to model a no-slip condition (i.e., perfect bonding) between the implant and the Sawbones® block. The impression coping abutment was modeled in approximately the exact dimensions. It was connected to the implant via a no-slip condition. The material of the impression coping abutment was titanium alloy. After the models were created, a modal analysis was conducted to calculate natural frequencies and mode shapes of the simulated test samples.

Results

Figure 16:
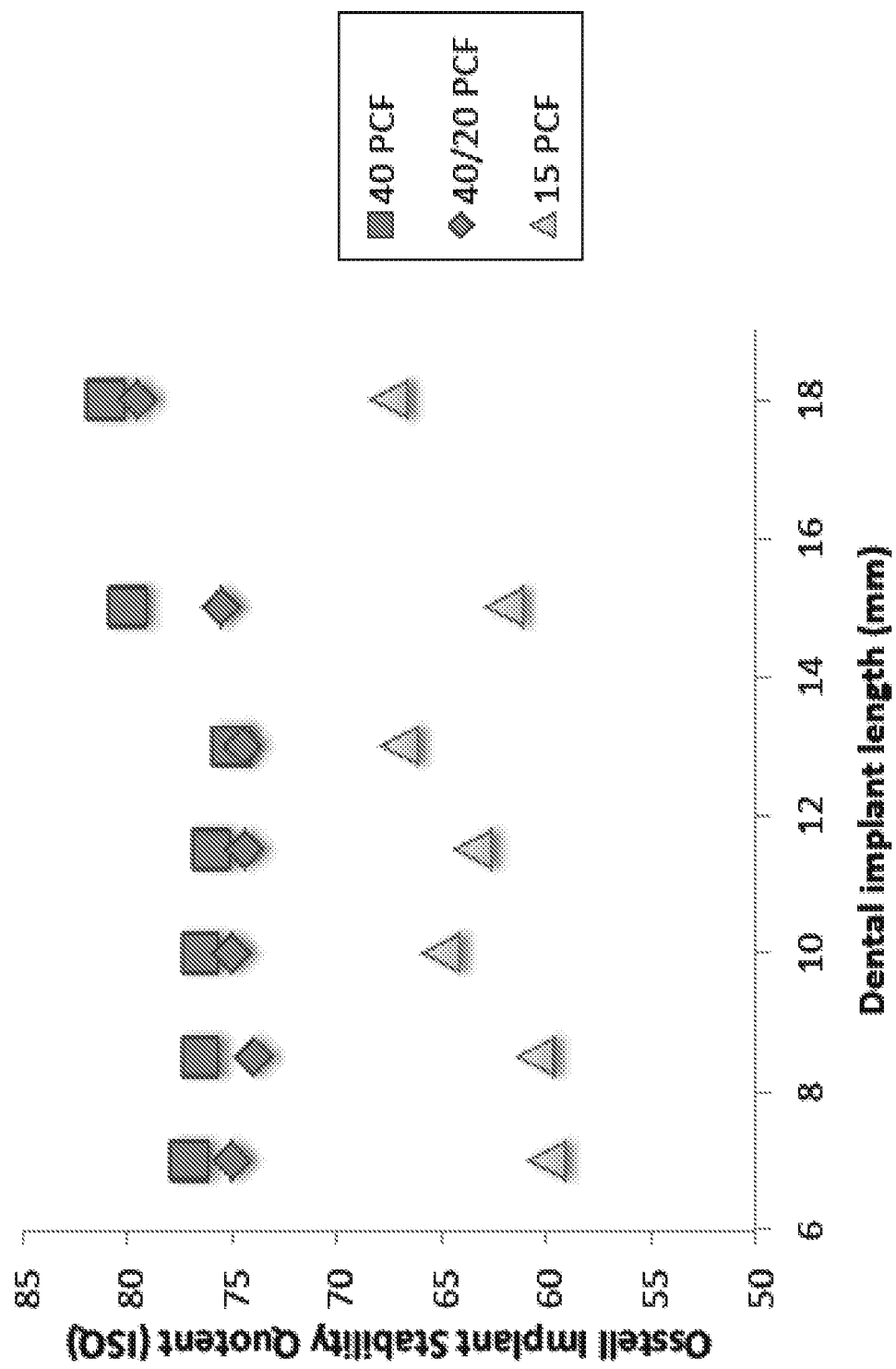
FIG. 16 is a graph showing the mean Ostell ISQ® measured for blocks of different densities, according to an example embodiment.

Ostell ISQ® Measurements:

The mean MD readings ranged between 75 to 81 for the high-density blocks, 74 to 79.5 for the hybrid blocks, and 60-67.5 for the low density blocks, as shown in FIG. 16. The ISQ values for the hybrid and high-density blocks are within the same range, while the ISQ values for the low-density blocks are lower. In other words, the ISQ values for the hybrid blocks are closer to the values of the high-density blocks than those of the low-density blocks. The measured ISQ readings represent implant stability according to the manufacturer. A closer look of the data, however, reveals several subtle observations. First of all, for the hybrid and high-density blocks, the mean ISQ reading is about the same for implants whose length is 13 mm or less. Then the ISQ reading starts to scatter when the implant length is greater than 13 mm. For the low-density blocks, the ISQ readings are very scattered.

Figure 17:
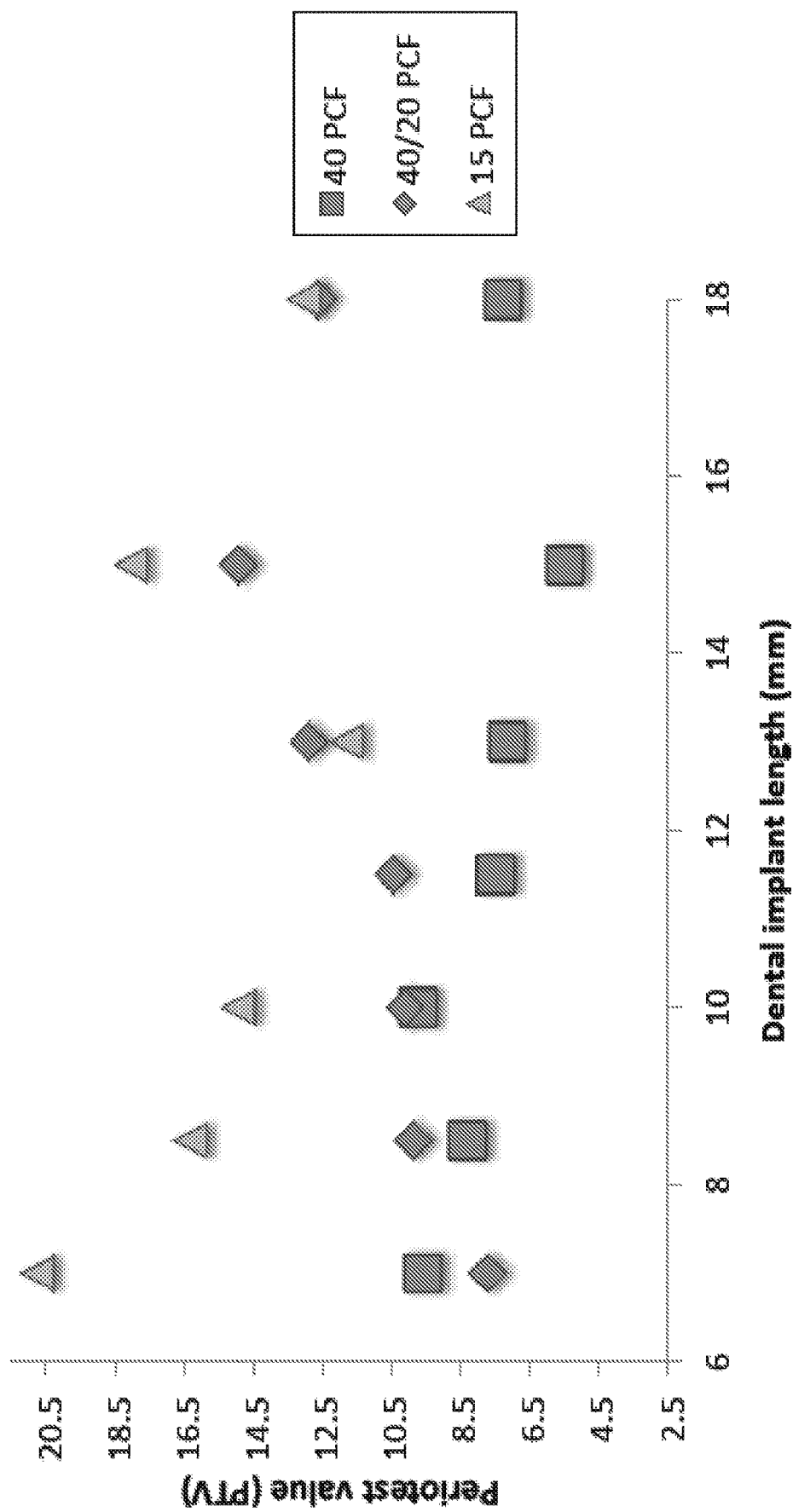
FIG. 17 is a graph showing Periotest® values (PTV) measured for blocks of different densities, according to an example embodiment.

Periotest® PTV Measurements:

According to the Periotest® guidelines, the lower the PTV reading is the higher the stability. The mean PTV readings ranged between 9.6 to 5.5 for the high-density blocks, 14.95 to 7.7 for the hybrid blocks, and 20.5 to 11.5 for the low-density blocks, as shown in FIG. 17. For the hybrid blocks, the PTV readings had a correlation coefficient of 0.84 implying that the longer the implant the less the stability. For the high-density block group, the correlation coefficient was −0.74 implying that the longer the implant the more stable it is. For the low-density group, the PTV readings had a correlation coefficient of −0.47 indicating a slight correlation between implant length and stability. In general, the PTV readings are very scattered and the measurements are not conclusive. The readings for the different density blocks are haphazard and do not follow a consistent pattern. Nevertheless, PTV readings for high-density blocks were much lower than that of the low-density blocks. According to the Periotest® guidelines, the values obtained from these measurements indicate implant instability because they are all higher than 0, as shown in FIG. 17.

Figure 18C:
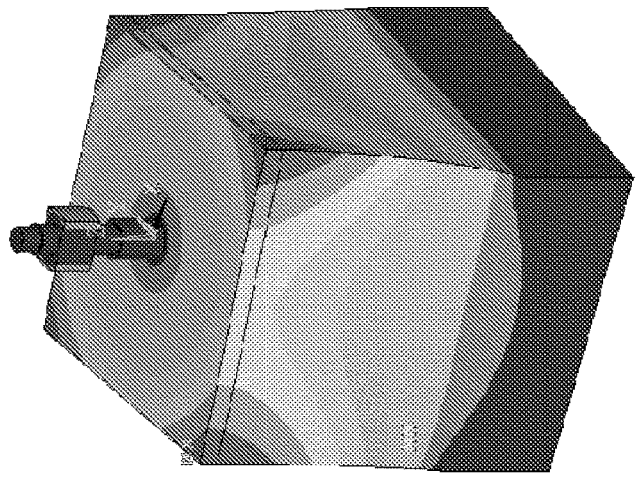
FIG. 18C is a three-dimensional finite element model of the dental implant of FIG. 18A in a third vibration mode, according to an example embodiment.
Figure 18B:
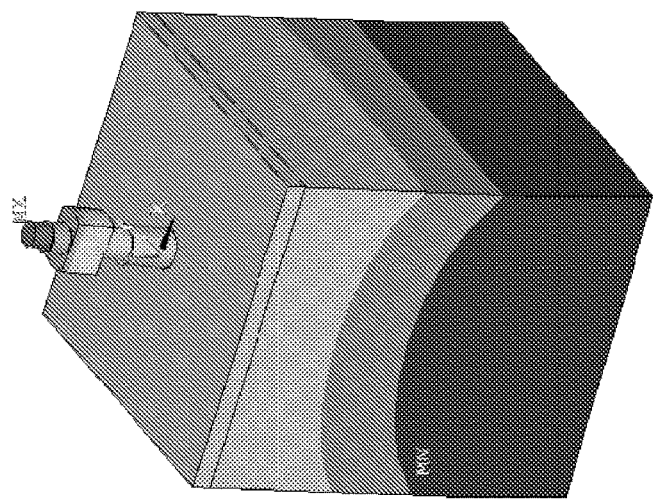
FIG. 18B is a three-dimensional finite element model of the dental implant of FIG. 18A in a second vibration mode, according to an example embodiment.
Figure 18A:
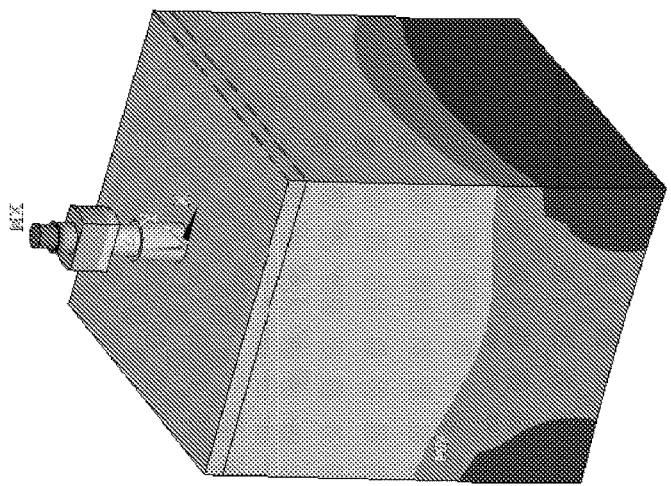
FIG. 18A is a three-dimensional finite element model of a dental implant embedded in a block in a first vibration mode, according to an example embodiment.

Finite Element Analysis:

Three major vibration modes were seen, as shown in FIGS. 18A-18C. The first mode, shown in FIG. 18A, represents a forward and backward movement of the abutment-implant assembly. Since the motion occurs in a direction parallel to the two sides that are partially fixed (as the boundary conditions), the block experiences relatively minor strain leading to a smaller stiffness. Therefore, this mode has the lowest natural frequency. The second mode, shown in FIG. 18B, stands for a sideways movement of the abutment-implant assembly. In the second mode, the motion occurs in a direction normal to the two sides that are partially fixed. Therefore, the block experiences relatively larger strain resulting in a higher stiffness and higher natural frequency. The third mode, shown in FIG. 18C, represents a twisting motion of the Sawbones®. Each vibration mode has its own natural frequency.

Figure 19:
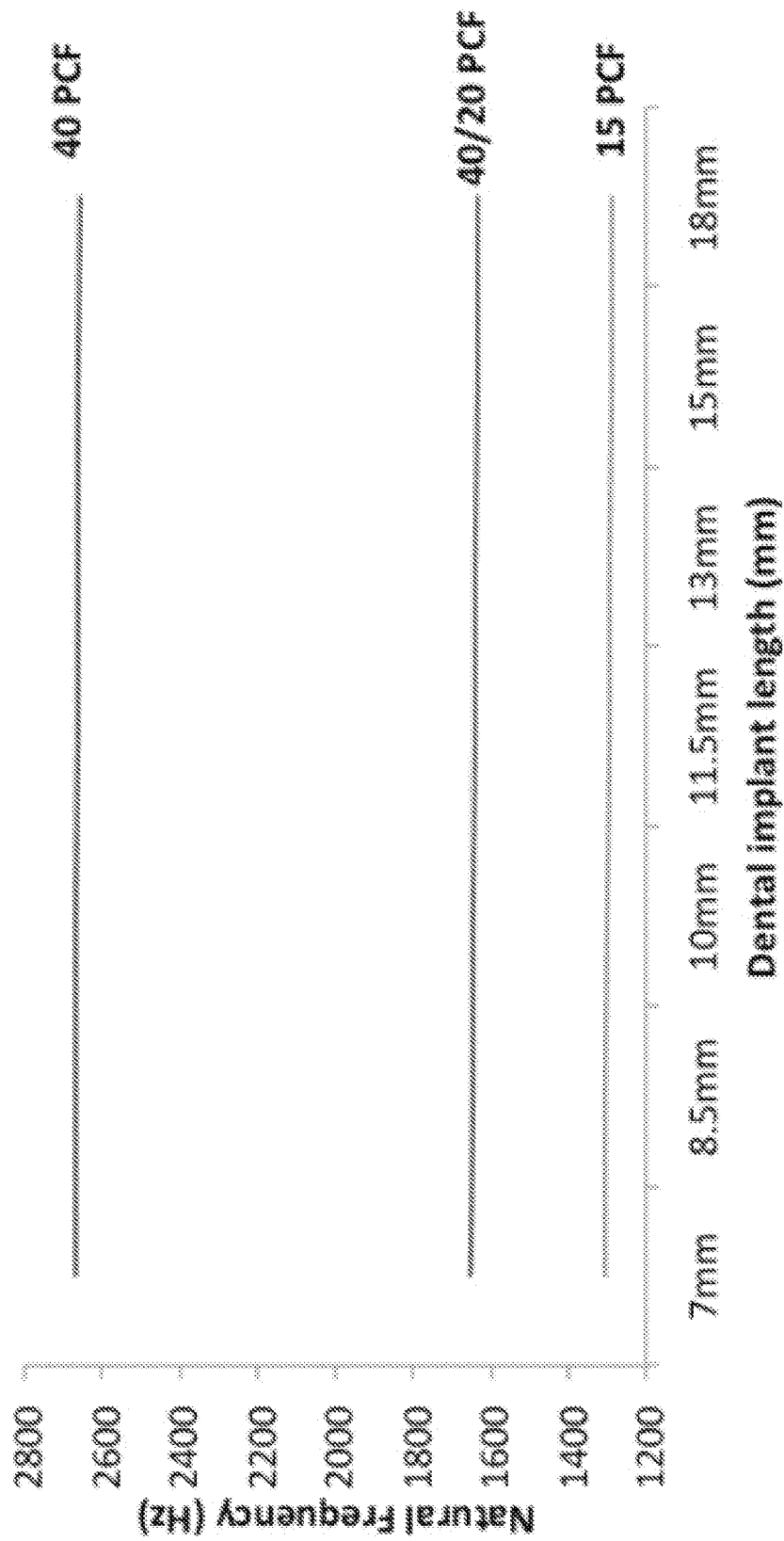
FIG. 19 is a graph showing finite element analysis predictions of the natural frequency based on the vibration of the dental implant, according to an example embodiment.

Based on the calculations of the first natural frequency, there are two major findings. First, the predicted natural frequency was independent of the implant length, as shown in FIG. 19. Second, the predicted natural frequency was highest for the 40 PCF blocks and the lowest for the 15 PCF blocks. Moreover, the frequency difference between the 15

PCF and 40/20 PCF blocks is small, while the frequency difference between the 40 PCF and 40/20 PCF blocks is more significant.

Experimental Modal Analysis:

The results of EMA had the same trend as the predictions from FEA. Three resonance peaks were seen in measured frequency response functions, confirming the three vibration modes predicted in FEA. Moreover, the frequencies at which the three resonance peaks appeared were measured natural frequencies. The presence of multiple natural frequencies manifests itself in the complex dynamics of the implant-Sawbones system.

Figure 20:
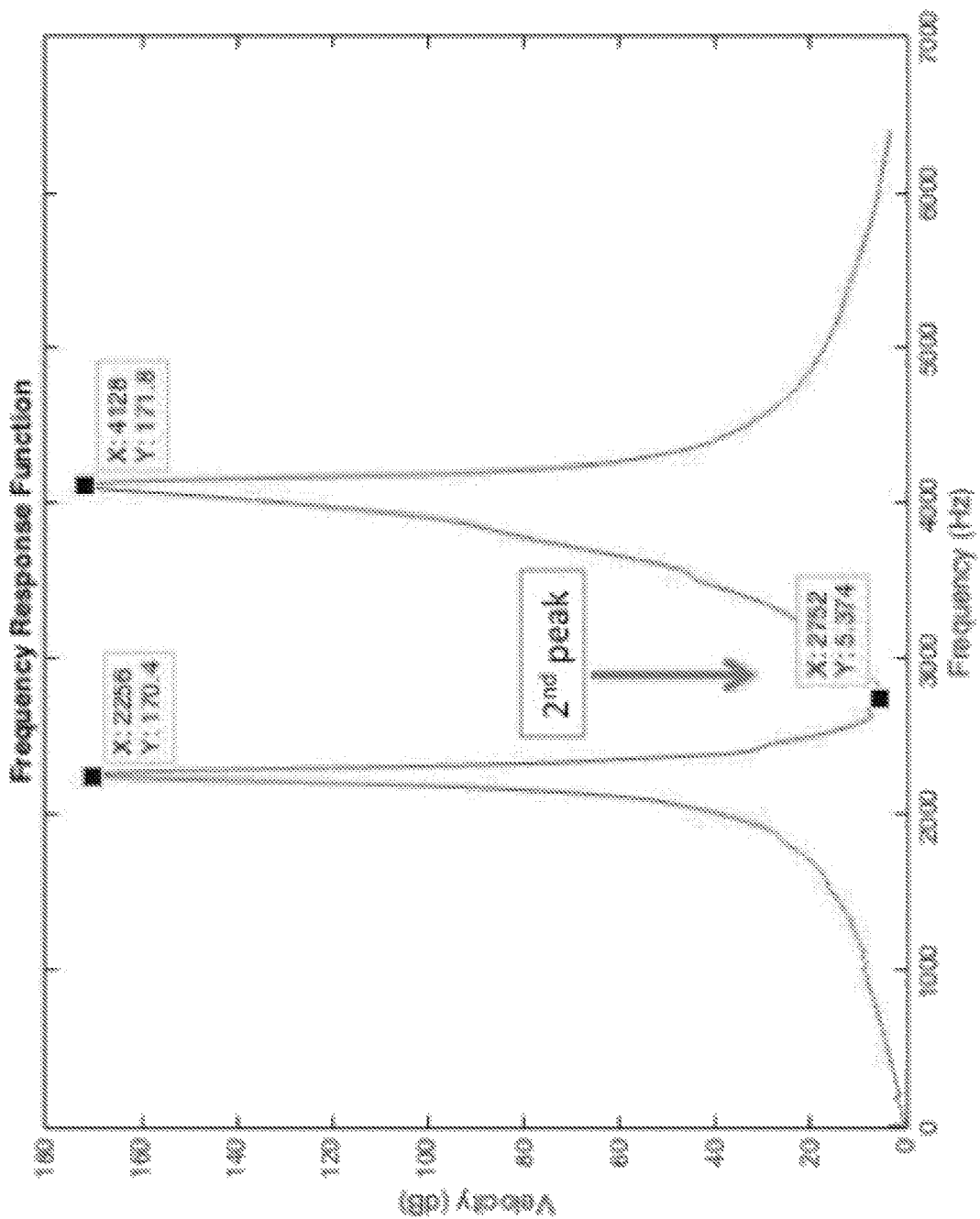
FIG. 20 is a graph showing a frequency response function of the abutment-dental implant system, according to an example embodiment.

To better excite the first mode, the hammer was adjusted such that it hit the abutment from the front as much as possible. This arrangement minimized excitations from the side and reduced the amplitude of the second peak. Such an arrangement was very desirable, because the second mode would not interfere with the first mode and contaminate the measured data. As a result, focus could be placed on the first mode, which was the most important mode. When a flawless experiment was conducted, the second peak could not be seen clearly because the second mode was not excited at all, as shown in FIG. 20.

Figure 21:
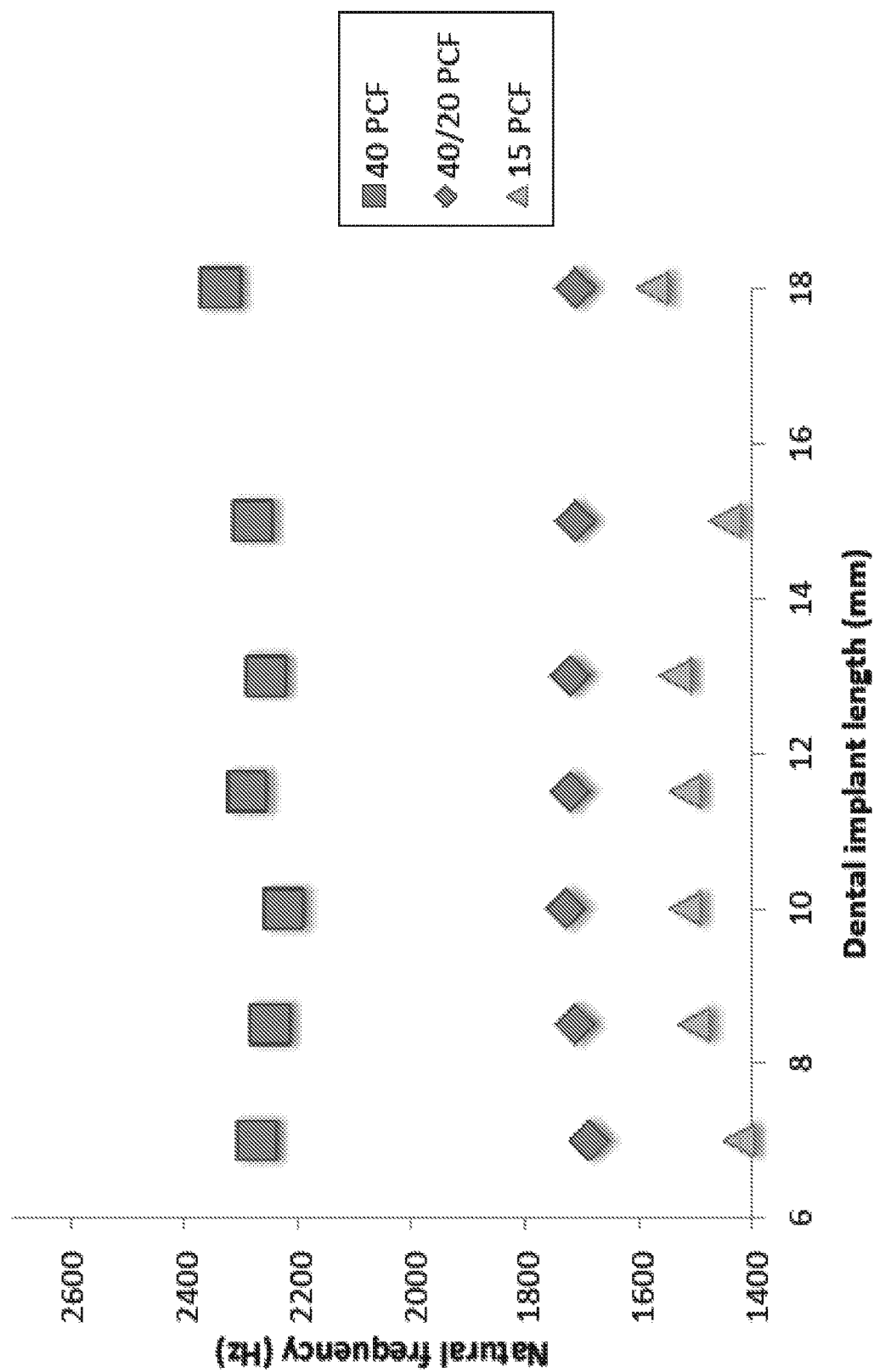
FIG. 21 is a graph showing measured natural frequency results from experimental modal analysis, according to an example embodiment.

The measured frequency values were very consistent. In general, the measured values of the first natural frequency ranged between 2224 Hz and 2336 Hz for the high-density blocks, between 1688 Hz and 1720 Hz for the hybrid blocks, and between 1424 Hz and 1576 Hz for the low-density blocks, as shown in FIG. 21. The measured natural frequency did not vary considerably with respect to the implant length as predicted in FEA. The measured frequency difference between the hybrid blocks and the low-density blocks was much smaller than between the hybrid blocks and the high-density blocks. These results make sense, since the low-density blocks are 15 PCF while the majority of the hybrid blocks are 20 PCF. The hybrid blocks should perform more like the low-density blocks, and the experimental results support that notion.

These experimental results agree very well with the predictions from the FEA not only qualitatively but also quantitatively, as shown by comparing FIG. 19 with FIG. 21. It should be noted that Sawbones® has a ±10% tolerance in physical properties, which could subsequently affect the measured natural frequencies.

E. ILLUSTRATIVE PROBES

As described above in relation to FIG. 1, a system for detecting stability of a medical implant may include (i) a probe configured to detect a response signal associated with a vibration of the medical implant in response to a force applied to the medical implant, and (ii) a computing device in communication with the probe, wherein the computing device is configured to perform one or more of the method steps discussed above in relation to FIG. 2. FIGS. 22-27 illustrate various probes that may be used to generate forces applied to the medical implant and detect a response signal associated with a vibration of the medical implant in response to the applied force. In the embodiments shown in FIGS. 22-26, the medical implant comprises a dental implant 302 positioned in the bone 304 of the patient. An abutment 306 is coupled to the dental implant 302 via threads 308. A dental crown 310 is then positioned over the abutment 306. Determining the stability of the dental implant 302 using any of the methods described herein may comprise applying a force directly to the dental implant 302, applying a force to the abutment 306, and/or applying a force to the dental crown 310. The medical implant illustrated in FIGS. 22-26 is not meant to be limiting, and the embodiments described herein apply to any medical implant, such as a dental implant, a dental crown, a dental restoration, a bone screw, a plate, a hip implant, or a knee implant, as non-limiting examples.

Figure 22:
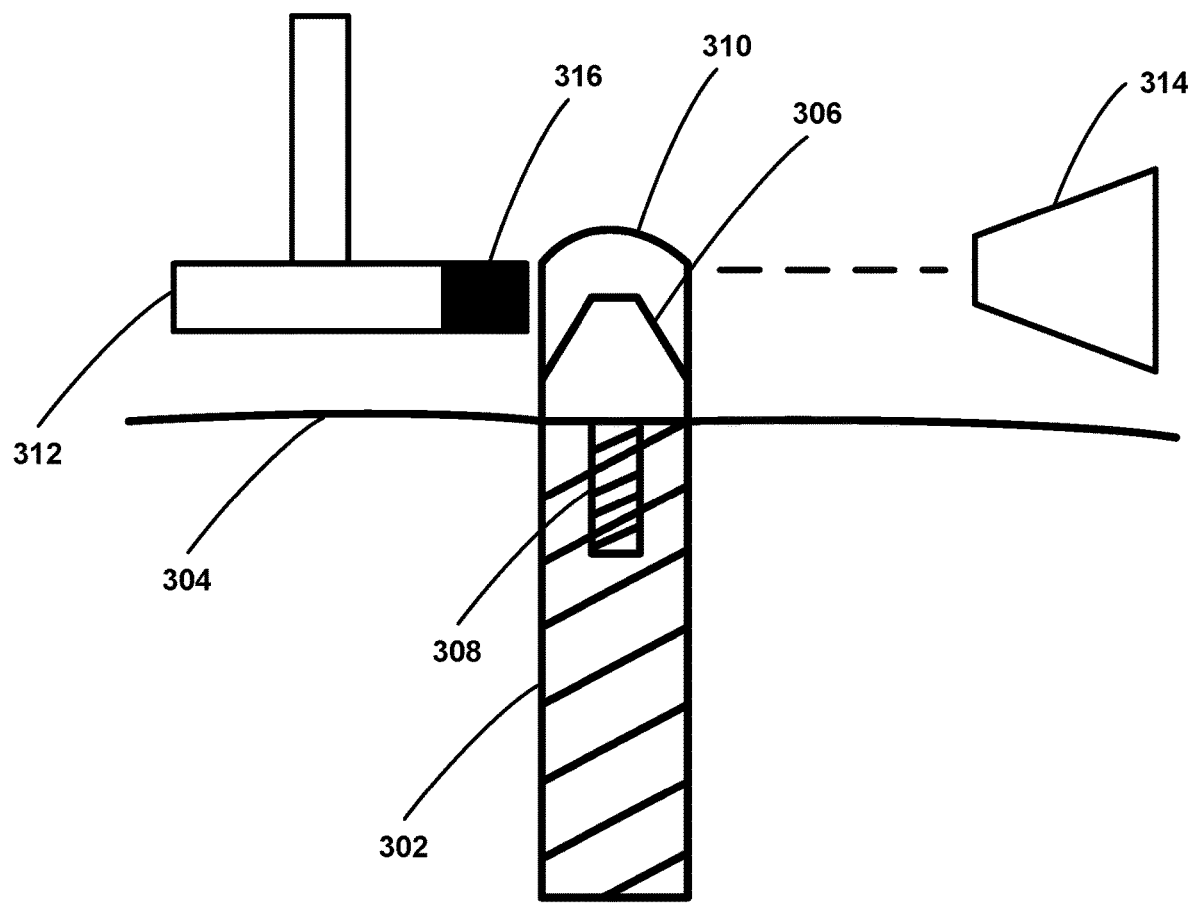
FIG. 22 illustrates a probe configured to detect a response signal associated with a vibration of a medical implant, according to an example embodiment.

FIG. 22 shows a first embodiment of components for obtaining the response signal. In the shown embodiment, the components include a hammer 312 as a force input source and a laser Doppler vibrometer 314 to generate a velocity output. In such an example, the hammer 312 comprises the probe. The hammer 312 is aligned and sized to tap a target object, such as an abutment 306 coupled to a dental implant 302 or a dental crown 310 coupled to the abutment 306, causing the dental implant 302 to vibrate. At the tip of the hammer 312, a load cell 316 serves as a force sensor to measure the force acting on the target object. The load cell 316 may be a piezoelectric sensor or piezoelectric block, positioned between a first surface of the hammer 312 and a location on the object at which the hammer 312 and load cell 316 contact the target object. The electrical charge of the block may be measured to provide an indication of force acting on the target object. At the same time, the vibrometer 314 measures the vibration velocity of the target object, which includes the dental implant 302, the abutment 306, and the dental crown 310 in this example. Such a vibrometer 314 is one type of optical sensor, though other optical and non-optical sensors may be used to measure vibration. The measured force and velocity data are fed into a spectrum analyzer, where a frequency response function is calculated in the frequency domain. Such an analyzer may be analyzer 118 as shown in FIG. 1. Various parameters (e.g., natural frequencies, viscous damping factors, and stiffness) can be extracted from the measured frequency response function. For the present disclosure, the natural frequencies and linear stiffness of the medical implant are determined, such as discussed with step 204 of FIG. 2.

Figure 23:
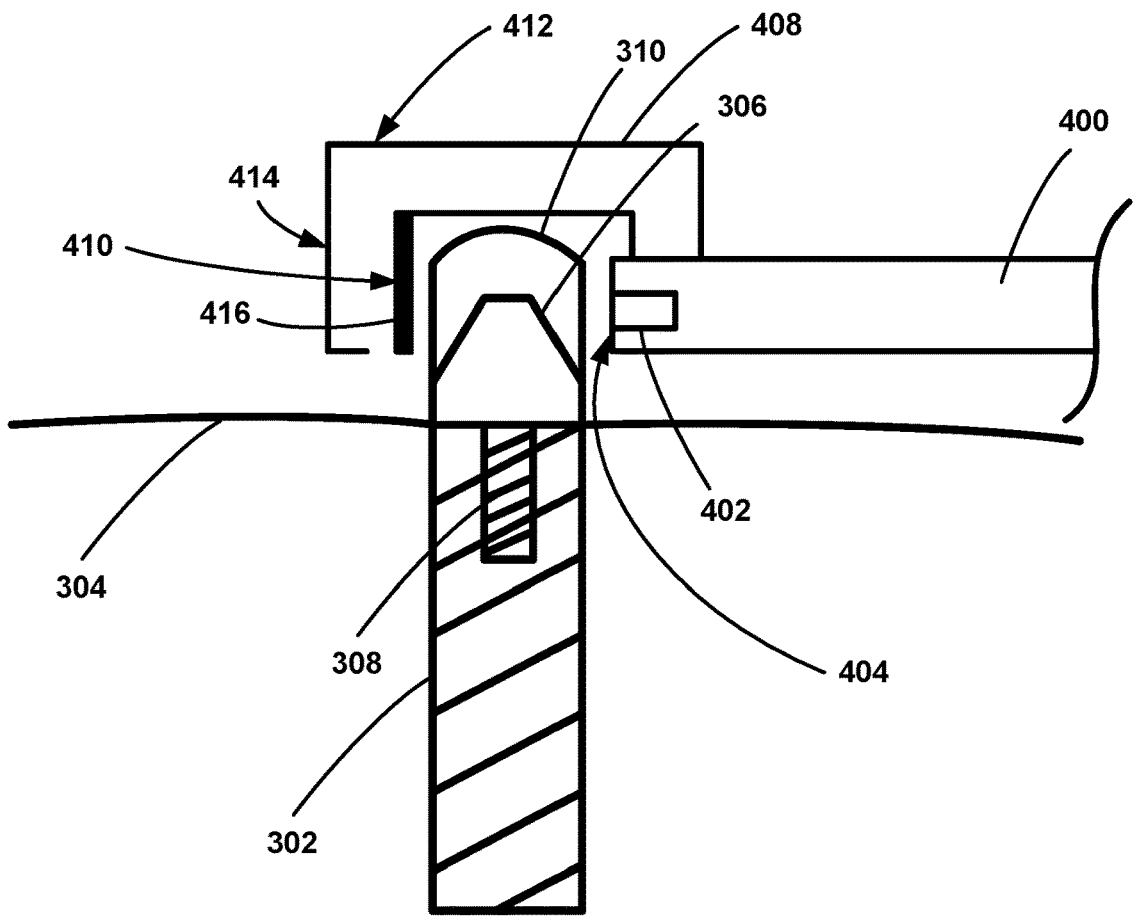
FIG. 23 illustrates another probe configured to detect a response signal associated with a vibration of a medical implant, according to an example embodiment.

FIG. 23 illustrates alternate embodiment of a probe 400. Such an embodiment includes a probe 400 with an actuator 402, such as a piezoelectric ceramic block, which simultaneously serves as a force transducer, positioned on a first surface 404 at a distal end of the probe 400 and configured to be placed in contact with a target object, such as the dental crown 310 shown in FIG. 23. When a voltage is applied to the piezoelectric actuator 402, it deforms and moves the dental crown 310, causing the dental implant 302 to vibrate. As discussed above, the target object may also be the dental implant 302, the abutment 306, or any other medical implant. The force exerted by the actuator 402 on the dental crown 310 may be estimated by the electric current going through the piezoelectric actuator 402, for example. The probe 400 also includes a support structure 408 physically coupled to the probe 400 and providing a second surface 410 spaced apart from and opposite the first surface 404. The probe 400 is further shaped to receive the dental crown 310 between the first surface 404 and second surface 410. The object 406 may be a medical implant, such as the dental implant shown in FIG. 23.

As such, the support structure 408 is configured to physically couple the probe 400 to a side of the dental crown 310, opposite a location at which the actuator 402 is configured to contact the dental crown 310. Such a support structure 408 may include a first portion 412 that extends a distance above and beyond the dental crown 310. The support structure 408 may also include a second portion 414 that extends from the first portion 412 at a substantially perpendicular angle, wherein the second portion 414 is configured to contact the opposite side of the dental crown 310. Moreover, the second portion 414 may have a compliant surface 416 in contact with the dental crown 310 allowing the dental crown 310 to move under the force of the piezoelectric actuator 402.

A response signal may be detected in response to forces applied to the dental crown 310 by the actuator 402 in several ways. For one embodiment, the piezoelectric actuator 402 may serve as a vibration sensor. For example, the voltage and the current of the piezoelectric actuator 402 may be monitor to obtain impedance measurements from which natural frequencies or linear stiffness coefficient or both may be extracted. For another embodiment, the compliant surface 416 may be made of piezoelectric polymer, such as PVDF, serving as a sensor. The current of the piezoelectric actuator 402 and the charge of the piezoelectric polymer may be used to extract natural frequencies and linear stiffness coefficients. For the embodiments of FIGS. 23-27, it is noted that an associated computing device 102 may not need to include a spectrum analyzer 118. In these embodiments, the signals from the probe, such as the probe 400 shown in FIG. 23, may be received by the processor 112 and the stiffness coefficient may be directly calculated by this same element in the computing device 102.

Figure 24:
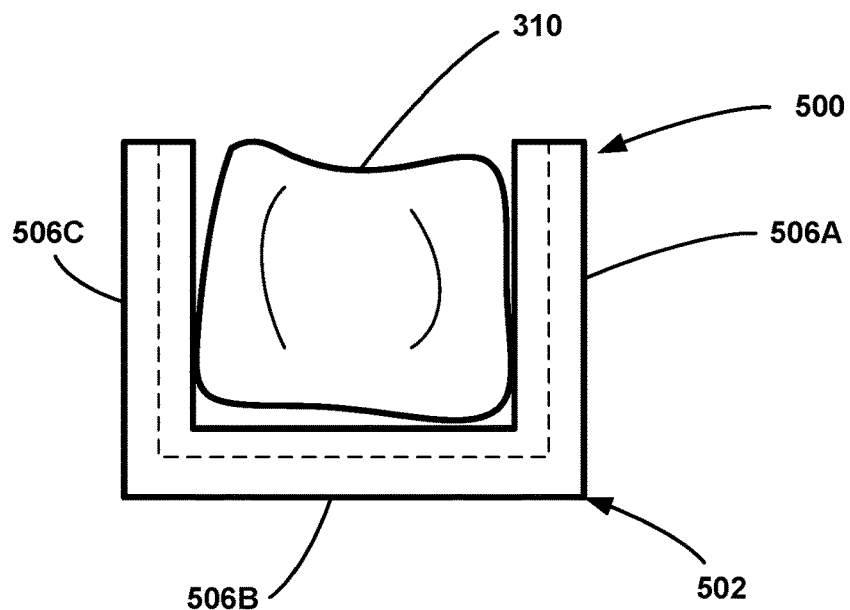
FIG. 24 illustrates another probe configured to detect a response signal associated with a vibration of a medical implant, according to an example embodiment.

FIG. 24 illustrates another embodiment of a probe 500. In this embodiment, the transducer 502, which may be a piezoelectric transducer, may be configured to be placed around two or more sides of a target object, such as the dental crown 310. As discussed above, the target object may also be the dental implant 302, the abutment 306, or any other medical implant. Application of a drive signal may cause the transducer 502 to vibrate, which in turn may cause the dental crown 310, the abutment 306, and the dental implant 302 to vibrate. The vibrations of the dental crown 310 may be detected by the same transducer 502 and converted into a response signal further usable as described elsewhere herein. Such a transducer may comprise an angled transducer having at least two portions, each portion coupled to another portion at an angle between about 70 degrees and about 110 degrees such that the dental crown 310 may be received between the coupled portions. In one particular example, as shown in FIG. 24, the transducer 502 includes three portions 506A, 506B, 506C interconnected at right angles so as to generally correspond to and enclose the dental crown 310.

Figure 25:
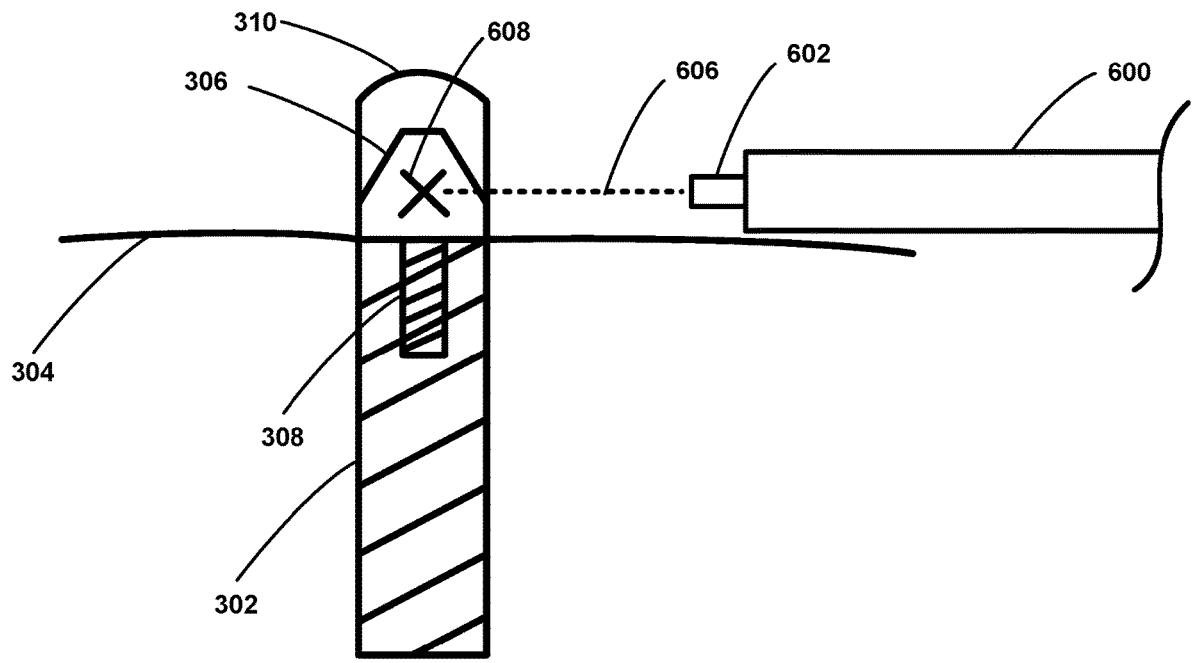
FIG. 25 illustrates another probe configured to detect a response signal associated with a vibration of a medical implant, according to an example embodiment.

FIG. 25 illustrates another embodiment of a probe 600. The embodiment of FIG. 25 is similar to FIG. 24, although the transducer 602 is positioned on only one side of the target object and at a distal end of the probe 600. In the example shown in FIG. 25, the target object is the dental crown 310. As discussed above, the target object may also be the dental implant 302, the abutment 306, or any other medical implant. In this embodiment, the transducer 602 may apply a mechanical force and detect a responsive mechanical vibration from the dental crown 310 (e.g., using impedance), converting the vibration into a responsive signal for subsequent processing. As such, the transducer 602 the transducer both applies a mechanical force to the dental crown 310 and detects a motion of the dental crown 310 in response to the mechanical force, and the response signal is determined based on the detected motion. A variation of this embodiment is to incorporate a laser guided system 606 to position the probe 600. Markers 608 may be made first on the dental crown 310. The laser system 606 finds a marker 608, and the probe is brought into contact with the dental crown 310 at that location to obtain a set of measurements. The process may be repeated for a plurality of markers to obtain measurements for the entire dental crown 310 that can be used to better extract angular stiffness via a computer model as discussed above in relation to FIG. 2.

Figure 26:
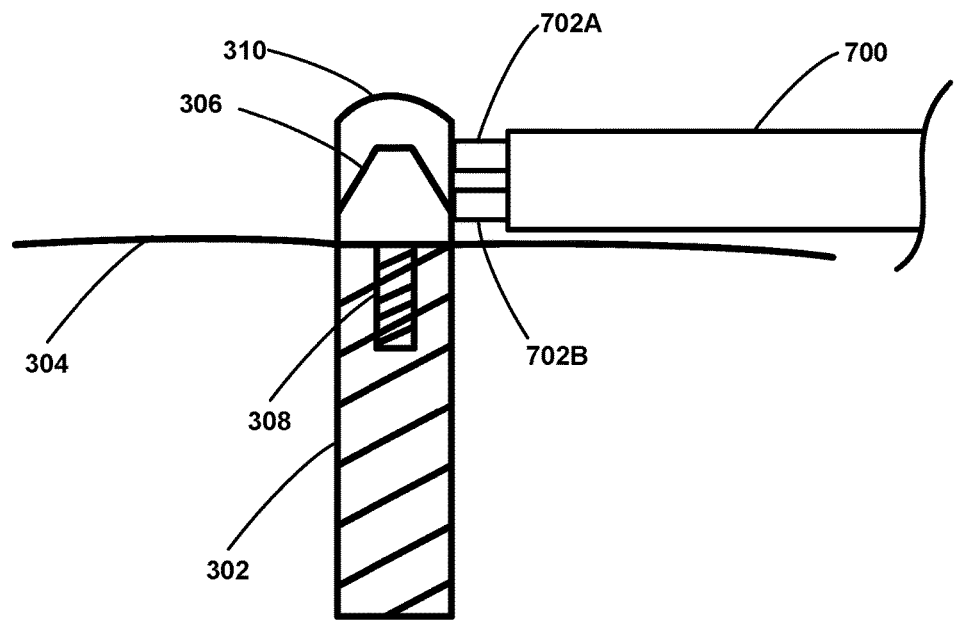
FIG. 26 illustrates another probe configured to detect a response signal associated with a vibration of a medical implant, according to an example embodiment.

FIG. 26 illustrates a further embodiment of a probe 700. In this embodiment, the probe 700 includes a pair of transducers 702A, 702B, such as piezo-blocks, at the distal tip of the probe 700. The two transducers 702A, 702B may be driven in an out-of-phase manner, such as by drive signal source 116, to generate angular excitation. In one particular example, the transducers 702A, 702B may be driven 180 degrees out of phase to generate the response signal. An impedance value may be measured by each transducer 702A, 702B. A difference of the measured impedances is proportional to the angular stiffness of the target object. In the example shown in FIG. 26, the target object is the dental crown 310. As discussed above, the target object may also be the dental implant 302, the abutment 306, or any other medical implant. Ideally, the centerline of the two transducers 702A, 702B should pass through the base of the dental crown 310, and the angular stiffness measured in this condition is the most accurate measurement. To obtain the ideal angular stiffness, a laser-guided system may be used to conduct the angular stiffness measurements at different locations, as discussed above in relation to FIG. 24. The ideal angular stiffness value can be obtained by extrapolating these measurements to the ideal position. A variation of this embodiment is to use one piezo-block 702A as an actuator while the other piezo-block 702B as a sensor to measure a frequency response curve similar to that shown in FIG. 23.

Figure 27:
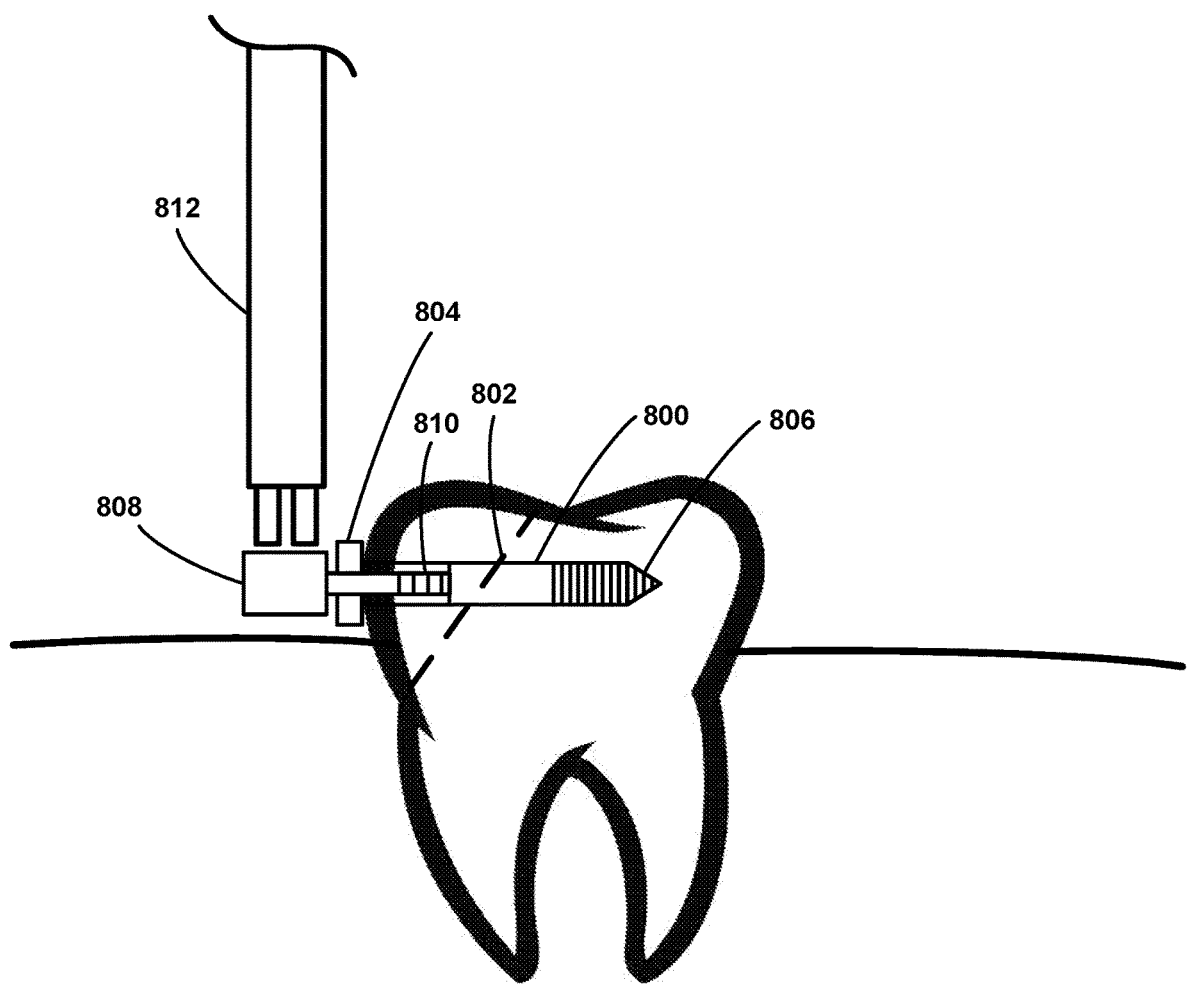
FIG. 27 illustrates another probe configured to detect a response signal associated with a vibration of a medical implant, according to an example embodiment.

FIG. 27 illustrates a bone screw 800 that brings two fractured bones 802 together. Although the example shown in FIG. 27 illustrates a fractured tooth, the example system and methods may apply to any fractured bone in a patient. The bone screw 800 has a cap portion 804 and a thread portion 806. The cap portion 804 and the thread portion 806 provide a preload and bring the fractured bones 802 tightly together to facilitate healing. After the bone screw 800 is tightened to secure the fractured bone 802, a removable abutment 808 is mounted onto the bone screw 800 via internal threads 810 inside the cap portion 804. The purpose of the removable abutment 808 is to provide a working space for measurement. Then a probe 812 (such as any of the probes described above in prior embodiments) is positioned against the removable abutment 808 to measure natural frequencies and/or linear stiffness coefficients of the bone screw 800 implanted inside the fractured bone 802. In the meantime, a finite element model of the fractured bone 802 including the bone screw 800 and the removable abutment 808 is created. Bone properties of the finite element model are adjusted so that the model predicts the measured natural frequencies and/or measured linear stiffness coefficients. Then the finite element model is used to calculate an angular stiffness at the cap portion 804 of the bone screw 800. The calculated angular stiffness thus quantifies the stability of the bone fixation. After the measurements, the removable abutment 808 is removed, and the fracture bone 802 is left to heal with the surrounding soft tissue under the effect of the bone screw 800.

F. EXAMPLE COMPUTER-READABLE MEDIUM

Figure 28:
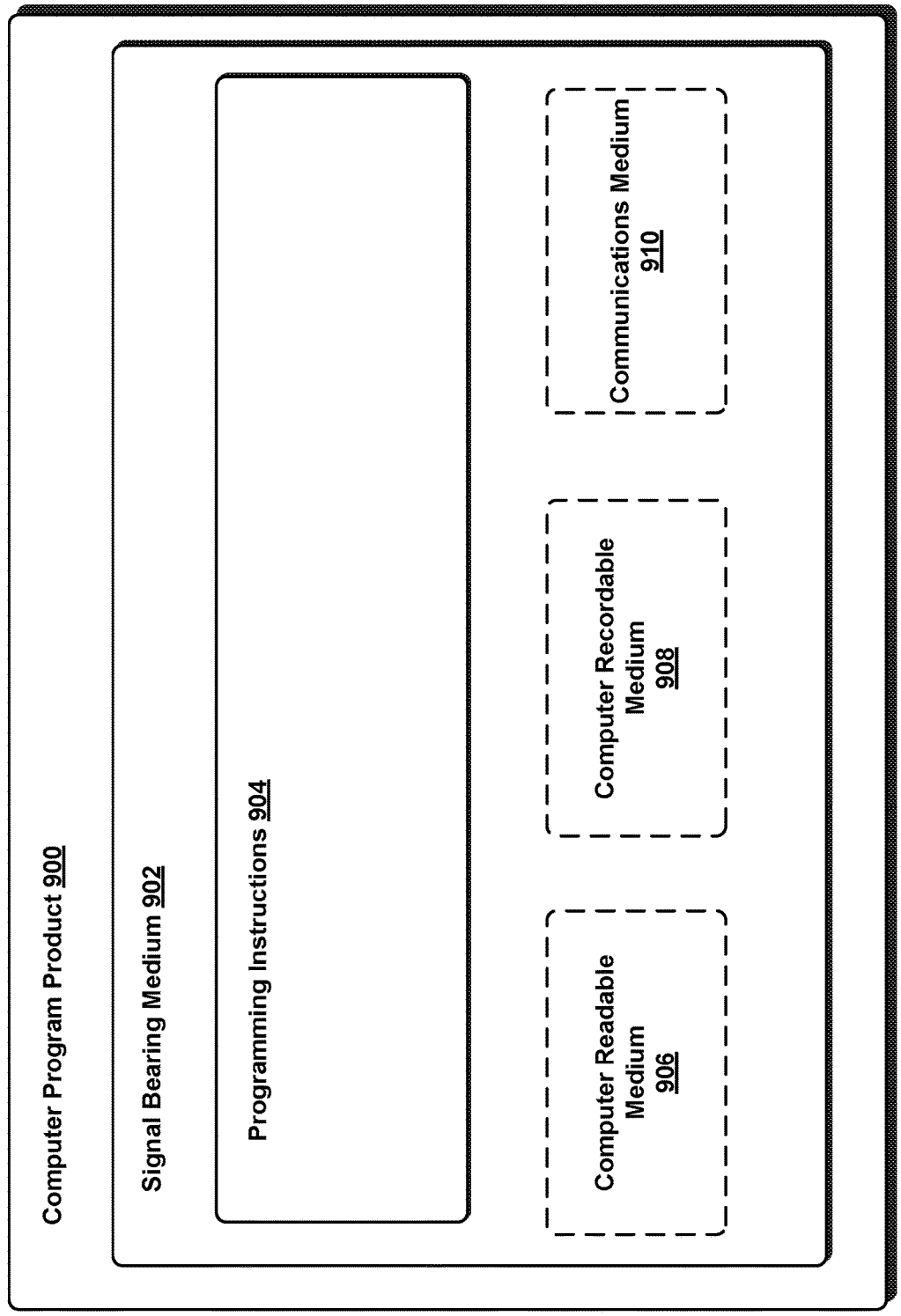
FIG. 28 depicts a computer-readable medium configured according to an example embodiment.

FIG. 28 illustrates a computer-readable medium configured according to an example embodiment. In example embodiments, the example system can include one or more processors, one or more forms of memory, one or more input devices/interfaces, one or more output devices/interfaces, and machine-readable instructions that when executed by the one or more processors cause the system to carry out the various functions, tasks, capabilities, etc., described above.

As noted above, in some embodiments, the disclosed methods can be implemented by computer program instructions encoded on a non-transitory computer-readable storage media in a machine-readable format, or on other non-transitory media or articles of manufacture. FIG. 28 is a schematic illustrating a conceptual partial view of an example computer program product that includes a computer program for executing a computer process on a computing device, arranged according to at least some embodiments presented herein.

In one embodiment, the example computer program product 900 is provided using a signal bearing medium 902. The signal bearing medium 902 may include one or more programming instructions 904 that, when executed by one or more processors may provide functionality or portions of the functionality described above with respect to the Figures. In some examples, the signal bearing medium 902 can be a computer-readable medium 906, such as, but not limited to, a hard disk drive, a Compact Disc (CD), a Digital Video Disk (DVD), a digital tape, memory, etc. In some implementations, the signal bearing medium 902 can be a computer recordable medium 908, such as, but not limited to, memory, read/write (R/W) CDs, R/W DVDs, etc. In some implementations, the signal bearing medium 902 can be a communications medium 910, such as, but not limited to, a digital and/or an analog communication medium (e.g., a fiber optic cable, a waveguide, a wired communications link, a wireless communication link, etc.). Thus, for example, the signal bearing medium 902 can be conveyed by a wireless form of the communications medium 910.

The one or more programming instructions 904 can be, for example, computer executable and/or logic implemented instructions. In some examples, a computing device such as the processor 112 of FIG. 1 is configured to provide various operations, functions, or actions in response to the programming instructions 904 conveyed to the processor 112 by one or more of the computer-readable medium 906, the computer recordable medium 908, and/or the communications medium 910.

The non-transitory computer-readable medium could also be distributed among multiple data storage elements, which could be remotely located from each other. The device that executes some or all of the stored instructions could be the probe 104 as illustrated in FIG. 1. Alternatively, the device that executes some or all of the stored instructions could be a server-side computing device.

G. CONCLUSION

The above detailed description describes various features and functions of the disclosed systems, devices, and methods with reference to the accompanying Figures. In the Figures, similar symbols typically identify similar components, unless context dictates otherwise. The illustrative embodiments described in the detailed description, Figures, and claims are not meant to be limiting. Other embodiments can be utilized, and other changes can be made, without departing from the scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

We claim:
1. A method for detecting stability of a medical implant, the method comprising:
    applying a force to the medical implant with a probe;
    based on the applied force, measuring a vibration of the medical implant via a vibration sensor;
    comparing the measured vibration of the medical implant based on the applied force with a natural frequency value or a linear stiffness coefficient predicted by a computer model of the medical implant; and
    based on the comparison, determining an angular stiffness coefficient of the medical implant, wherein the angular stiffness coefficient corresponds to a stiffness of a rotation about an axis perpendicular to a centerline of the medical implant, and wherein the angular stiffness coefficient indicates a stability of the medical implant.

2. The method of claim 1, wherein applying the force to the medical implant comprises generating a driving signal to excite the medical implant into vibration, wherein the vibration of the medical implant is based on the excited vibration of the medical implant in response to the driving signal.

3. The method of claim 1, wherein the computer model is a finite element model of the medical implant.

4. The method of claim 1, wherein the medical implant includes a longitudinal axis extending from a first surface of the medical implant to a second surface opposite the first surface, wherein the medical implant includes a second axis that is perpendicular to the longitudinal axis, and wherein the centerline of the medical implant is parallel to the longitudinal axis.

5. The method of claim 4, wherein the second surface of the medical implant is implanted in a bone.

6. The method of claim 1, wherein the medical implant comprises at least one of a dental implant, a dental crown, a dental restoration, a bone screw, a plate, a hip implant, or a knee implant.

7. The method of claim 1, further comprising:
    removably coupling an abutment to the medical implant, wherein the force is applied indirectly to the medical implant by applying the force to the abutment.

8. The method of claim 1, further comprising:
    providing a binary indication of whether or not the medical implant is stable.

9. The method of claim 1, further comprising:
    providing a notification of a degree of stability of the medical implant based on the determined angular stiffness coefficient of the medical implant.

10. A non-transitory computer-readable medium having stored thereon instructions that, when executed by one or more processors of a computing device, cause the computing device to perform functions comprising the method steps of claim 1.

11. A system for detecting stability of a medical implant, the system comprising:
    a probe configured to measure a force applied to the medical implant and a vibration of the medical implant based on the applied force; and
    a computing device in communication with the probe, wherein the computing device is configured to:

compare the measured vibration based on the applied force with a computer model of the medical implant; and based on the comparison, determine an angular stiffness coefficient of the medical implant, wherein the angular stiffness coefficient corresponds to a stiffness of a rotation about an axis perpendicular to a centerline of the medical implant, and wherein the angular stiffness coefficient indicates a stability of the medical implant.

12. The system of claim 11, wherein the computing device is configured to generate a driving signal applied to the medical implant by the probe to excite the medical implant into vibration, and wherein the vibration of the medical implant is based on the excited vibration of the medical implant in response to the driving signal.

13. The system of claim 11, wherein probe comprises a vibration sensor.

14. The system of claim 13, wherein the vibration sensor is an optical sensor.

15. The system of claim 11, wherein the probe comprises:
a transducer on a first surface at a distal end of the probe; and
a support structure physically coupled to the probe and providing a second surface spaced apart from and opposite the first surface, wherein the probe is further shaped to receive the medical implant between the first surface and second surface.

16. The system of claim 11, wherein the probe comprises an angled transducer having at least two portions, each portion coupled to another portion at an angle between about 70 degrees and about 110 degrees such that the medical implant may be received between the coupled portions.

17. The system of claim 11, wherein the probe comprises a transducer on a first surface at a distal end of the probe, wherein the transducer both applies a mechanical force to the medical implant and detects a motion of the medical implant in response to the mechanical force, wherein the vibration of the medical implant is determined based on the detected motion.

18. The system of claim 11, wherein the probe comprises a first transducer and a second transducer positioned on a first surface of the probe at a distal end of the probe, wherein the computing device is further configured to drive the first transducer and the second transducer out of phase to generate the vibration of the medical implant.

* * * * *